(12) United States Patent
Cordero et al.

(10) Patent No.: US 11,229,167 B2
(45) Date of Patent: Jan. 25, 2022

(54) PLANTS AND METHODS FOR HIGH DENSITY PLANT PRODUCTION

(71) Applicant: MONSANTO TECHNOLOGY LLC, St. Louis, MO (US)

(72) Inventors: Juan Cordero, St. Louis, MO (US); Daniel Ovadya, St. Louis, MO (US); Kyle B. Smith, St. Louis, MO (US); Adrian Vargas, St. Louis, MO (US)

(73) Assignee: MONSANTO TECHNOLOGY LLC, St. Louis, MO (US)

( * ) Notice: Subject to any disclaimer, the term of this patent is extended or adjusted under 35 U.S.C. 154(b) by 122 days.

(21) Appl. No.: 16/470,054

(22) PCT Filed: Dec. 15, 2017

(86) PCT No.: PCT/US2017/066623
§ 371 (c)(1),
(2) Date: Jun. 14, 2019

(87) PCT Pub. No.: WO2018/112318
PCT Pub. Date: Jun. 21, 2018

(65) Prior Publication Data
US 2019/0357455 A1    Nov. 28, 2019

Related U.S. Application Data

(60) Provisional application No. 62/435,209, filed on Dec. 16, 2016.

(51) Int. Cl.
| | | |
|---|---|---|
| *A01G 24/00* | (2018.01) | |
| *A01G 22/50* | (2018.01) | |
| *A01G 7/06* | (2006.01) | |
| *A01G 25/00* | (2006.01) | |
| *A01H 1/00* | (2006.01) | |

(52) U.S. Cl.
CPC ............. *A01G 22/50* (2018.02); *A01G 7/06* (2013.01); *A01G 25/00* (2013.01); *A01H 1/12* (2021.01)

(58) Field of Classification Search
USPC ................................................. 47/50.1, 58.1
See application file for complete search history.

(56) References Cited

U.S. PATENT DOCUMENTS 6,184,440 B1 *   2/2001   Shoseyov et al. ..... C07K 14/33
                                                          800/290

FOREIGN PATENT DOCUMENTS

| CN | 103109619 A | 5/2013 |
|---|---|---|
| CN | 104902750 A | 9/2015 |
| CN | 105230179 A | 1/2016 |
| CN | 105874967 A | 8/2016 |

OTHER PUBLICATIONS

Du et al. Water use and yield responses of cotton to alternate partial root-zone drip irrigation in the arid area of north-west China Irri. Sci (2008) 26:147-159.*
Reddy et al. Carbon dioxide and temperature effects on Pina Cotton development. Agron. J. 87:820-826 (1995).*
Hejnak et al. Growth and photosynthesis of Upland and Pima cotton: response to drought and heat stress Plant Soil Environ. vol. 61 2015 No. 11:507-514.*
Du et al., "Water use and yield responses of cotton to alternate partial root-zone drip irrigation in the arid area of north-west China", Irrig Sci, 2008, pp. 147-159, 26.
Reddy, K.R., et al., "Carbon Dioxide and Temperature Effects on Pima Cotton Development," Agronomy Journal, Jan. 1995, pp. 820-826, vol. 87.
Reddy et al., "Temperature Effects on Early Season Cotton Growth and Development", Agronomy Journal, Mar. 1992, pp. 229-237, vol. 84.
Du et al., "Effect of Alternate Partial Root-Zone Drip Irrigation on Yield and Water Use Efficiency of Cotton", Scientia Agricultura Sinica, 2005, pp. 2061-2068, vol. 38, No. 10.

* cited by examiner

*Primary Examiner* — Annette H Para
(74) *Attorney, Agent, or Firm* — Thompson Coburn LLP; Chunping Li; William A. Holtz

(57) ABSTRACT

Provided are methods for growing a plant under certain stressed conditions that alter the morphology of the plant. In certain aspects, however, although the plant is altered and may be undesirable for commercial purposed, the plant still produces an adequate number of seeds for breeding purposes. Further, because plants may be smaller in size, they can be grown at higher densities, allowing the production of large populations of plants to be brought under controlled conditions which can exclude pollinating insects and thus increase the genetic purity achievable in a breeding program.

12 Claims, 10 Drawing Sheets

PLANTS AND METHODS FOR HIGH DENSITY PLANT PRODUCTION

CROSS-REFERENCE TO RELATED APPLICATIONS

This is a U.S. National Phase application of PCT Application Serial No. PCT/US2017/066623, filed on Dec. 15, 2017, which claims the benefit of U.S. Provisional Application 62/435,209, filed on Dec. 16, 2016, each of which is incorporated herein by reference in its entirety.

BACKGROUND

The goal of plant cultivation is generally to provide growing conditions, such as irrigation, light, spacing, temperature and access to nutrients that promote healthy plant growth, including achieving a certain size and producing a number of seeds or fruit typical of a healthy plant. For example for cotton, which is shrubby plant that grows to be about 3 to 5 feet tall, typical commercial plantings have a plant density of about 8 to 12 plants per square meter with rows spaced about 1 meter apart. This spacing has been developed to optimize crop performance by generally increasing yield per unit area and minimizing disease susceptibility.

1 The large amount of space, however, needed to grow large populations of plants such as cotton is an obstacle to growing plants in controlled environments, such as green houses or grow houses, where not only can conditions such as temperature, light, and water be controlled, but the presence of pollinating insects minimized. This would be especially advantageous in breeding programs where the genetic purity resulting from crosses can be increased due to the lack of interference from pollinating insects. Increases in genetic purity translate into higher efficiencies and/or lower costs in breeding programs. Further the synchronization of flowering may also translate into higher efficiencies and/or lower costs in breeding programs by reducing overall cycle time and resource waste.

Therefore, there remains a need for methods of growing plants for use in more efficient breeding programs that are feasible in light of the space limitations.

SUMMARY

Provided herein are methods of producing a cotton seed by growing a cotton plant from a cotton seed under a stressed condition. It is understood that reference to "an aspect" refers to any of the methods disclosed herein and should not be limited to any particular method unless otherwise stated. In certain aspects, the stressed condition comprises growing the cotton plant in a volume of growth media of less than about 2,000 mL, less than about 1,500 mL, less than about 1,000 mL, less than about 500 mL, less than about 450 mL, less than about 350 mL, less than about 250 mL, or less than about 200 mL, for at least 40 days, for at least 50 days, for at least 60 days, for at least 70 days, for at least 75 days, or for at least 80 days during the time from when the cotton seed germinates to when the cotton plant produces at least one cotton boll that contains a seed, wherein the seed comprises at least one embryo with a cotyledon in the primordia stage and optionally wherein the seed comprises a black layer (restricted growth media volume). In certain aspects, the stressed condition comprises growing the cotton plant at a temperature of at least about 37° C., 38° C., 39° C., 40° C., 41° C., 42° C., 43° C., 44° C., 45° C., 46° C., 47° C., or 48° C., for at least about 2, 3, 4, 5, 6, 7, 8, 9, 10, 11, or 12 hours per day, for at least 40 days, for at least 50 days, for at least 60 days, for at least 70 days, for at least 75 days, or for at least 80 days during the time from when the cotton seed germinates to when the cotton plant produces at least one cotton boll that contains a seed, wherein the seed comprises at least one embryo with a cotyledon in the primordia stage and optionally wherein the seed comprises a black layer (high temperature). In certain aspects, the stressed condition comprises growing the cotton plant by providing less than about 500 mL, less than about 400 mL, less than about 300 mL, less than about 200 mL, less than about 100 mL, or less than about 50 mL of water per day on average, for at least 40 days, for at least 50 days, for at least 60 days, for at least 70 days, for at least 75 days, or for at least 80 days during the time from when the cotton seed germinates to when the cotton plant produces at least one cotton boll that contains a seed, wherein the seed comprises at least one embryo with a cotyledon in the primordia stage and optionally wherein the seed comprises a black layer (restricted irrigation). In certain aspects, the stressed condition can be a combination of any of these.

In certain aspects, the method comprises growing a cotton plant from a cotton seed under the stressed condition of: restricted growth media volume and/or restricted irrigation, wherein the cotton plant is also grown at a temperature of at least about 32° C., 33° C., 34° C., 35° C., or 36° C. for at least about 2, 3, 4, 5, 6, 7, 8, 9, 10, 11, or 12 hours per day, for at least 40 days, for at least 50 days, for at least 60 days, for at least 70 days, for at least 75 days, or for at least 80 days during the time from when the cotton seed germinates to when the cotton plant produces at least one cotton boll that contains a seed, wherein the seed comprises at least one embryo with a cotyledon in the primordia stage and optionally wherein the seed comprises a black layer.

In certain aspects, the days during which the cotton plant is grown under restricted growth media volume and/or restricted irrigation correspond to the days during which the plant is grown at a temperature of at least about 32° C., 33° C., 34° C., 35° C., 36° C., 37° C., 38° C., 39° C., 40° C., 41° C., 42° C., 43° C., 44° C., 45° C., 46° C., 47° C., or 48° C., for at least about 2, 3, 4, 5, 6, 7, 8, 9, 10, 11, or 12 hours a day. In certain aspects, the plant is grown at a nighttime temperature of about 18° C. to 22° C. In certain aspects, on at least about 50%, 60%, 70%, 80%, 90%, 95%, 98%, or 100% of the days on which the plant is grown at a temperature of at least about 37° C., 38° C., 39° C., 40° C., 41° C., 42° C., 43° C., 44° C., or 45° C., it is not grown at this temperature for more than about 6, 7, 8, 9, 10, 11, 12, 13, 14, 15, or 16, 18, or 20 hours per day. In certain aspects, on at least about 50%, 60%, 70%, 80%, 90%, 95%, 98%, or 100% of the days on which the plant is grown at a temperature of at least about 37° C., 38° C., 39° C., 40° C., 41° C., 42° C., 43° C., 44° C., or 45° C., the plant is also grown at a temperature of about 18° C. to 22° C. for at least 2, 3, 4, 5, 6, 7, 8, 9, 10, 11, 12, 13, 14, 15, or 16 hours per a day.

In certain aspects, the cotton plant is grown at least under the stress condition of restricted growth media volume. In certain aspects, the cotton plant is grown at least under the stress condition of high temperature. In certain aspects, the cotton plant is grown at least under the stress condition of restricted irrigation.

In certain aspects, the cotton plant grown under a stressed condition and having produced at least one cotton boll that contains a seed, wherein the seed comprises at least one embryo with a cotyledon in the primordia stage is of a diminished size, such as decreased in height, shortened internode length and/or having reduced biomass, compared to a control plant.

In certain aspects, the cotton plant is grown in a controlled environment.

In certain aspects, the cotton plant is grown in a volume of growth media of from any of about 200 mL, 250 mL, 300 mL, 350 mL, or 400 mL to any of about 300 mL, 350 mL, 400 mL, or 500 mL, for at least 40 days, for at least 50 days, for at least 60 days, for at least 70 days, for at least 75 days, or for at least 80 days during the time from when the cotton seed germinates to when the cotton plant produces at least one cotton boll that contains a seed, wherein the seed comprises at least one embryo with a cotyledon in the primordia stage and optionally wherein the seed comprises a black layer.

In certain aspects, the method further comprises applying a plant growth regulator (PGR) to the cotton plant before the first pinhead square stage. In certain aspects, the method further comprises applying a PGR to the cotton plant at a day not past 20 days, 21 days, 22 days, 23 days, or 25 days after germination. In certain aspects, the method comprises applying a PGR at 20 to 25 days after germination, 20 to 24 days after germination, 21 to 23 days after germination, or 22 to 24 days after germination. In certain aspects, the PGR is a compound known to inhibit the synthesis, update, or persistence of gibberellic acid in a plant. Further, In certain aspects, the PGR is selected from the group consisting of chlormequat-CL, mepiquat-CL, AMO-1618, clorphonium-Cl, tetcylacis, ancymidol, flurprimidol, paclobutrazol, uniconazole-P, inabenfide, prohexadione-CA, trinexapac-ethyl, daminozide, exo-16,17-, dihydro-GA5-13-acetate, systemin, phytosulfokine, and rapid alkalinization factor. And, in certain aspects, the PGR is mepiquat chloride.

In certain aspects, the cotton plant having produced at least one cotton boll that contains a seed, wherein the seed comprises at least one embryo with a cotyledon in the primordia stage, is less than about 30 inches tall, less than about 24 inches tall, less than about 18 inches tall, less than about 15 inches tall, or less than about 12 inches tall. In certain aspects, the cotton plant having produced at least one cotton boll that contains a seed, wherein the seed comprises at least one embryo with a cotyledon in the primordia stage, has at least 20 seeds, at least 30 seeds, at least 40 seeds, at least 50 seeds, or at least 60 seeds.

In certain aspects, the seed of the cotton plant grown under a stressed condition is used in a breeding program. Certain aspects comprise collecting at least one seed from the plant grown under a stressed condition. In certain aspects, the method further comprises testing at least one collected seed or a plant grown from the collected seed. The testing can be, for example, genotyping and/or phenotyping for genetic and/or physical characteristics and traits. In certain aspects, the method further comprises selecting a cotton plant to grow based on the testing. In certain aspects, the method further comprises crossing a cotton plant based on the testing.

In certain aspects, the cotton plant grown under a stressed condition is a member of a population of cotton plants grown at an average density of at least 10, 30, 60, 75, 100, 125, or 150 plants per square meter. In certain aspects, the population of plants comprises at least about 50 cotton plants, at least about 100 cotton plants, at least about 500 cotton plants, at least about 1,000 cotton plants, at least about 5,000 cotton plants, at least about 10,000 cotton plants, at least about 100,000 cotton plants, at least about 500,000 cotton plants, or at least about 1,000,000 cotton plants. Similarly, in certain aspects, the population of plants comprises 50 or more cotton plants, 100 or more cotton plants, 500 or more cotton plants, 1,000 or more cotton plants, 5,000 or more cotton plants, 10,000 or more cotton plants, 100,000 or more cotton plants, 500,000 or more cotton plants, or 1,000,000 or more cotton plants. In certain aspects, the cotton plant grown under a stressed condition is grown as a member of a population of cotton plants at an average density of at least 10, 30, 60, 75, 100, 125, or 150 plants per square meter, for at least 40 days, for at least 50 days, for at least 60 days, for at least 70 days, or for at least 80 days during the time from when the cotton seed germinates to when the cotton plant produces at least one cotton boll that contains a seed, wherein the seed comprises at least one embryo with a cotyledon in the primordia stage. In certain aspects, at least about 50%, 60%, 70%, 80%, 90%, 95%, 98%, or 99% of the cotton plants in the population have reaches a stage in their life cycle wherein pinhead squares have formed. In certain aspects, the population of plants is grown in a controlled environment.

Provided herein are methods of producing a population of cotton plants by: collecting at least one seed produced by a cotton plant grown under a stressed condition according to any of the aforementioned methods; testing (e.g., genotype and/or phenotype) at least one collected seed or plant grown from the collected seed; and growing and/or crossing a cotton plant based on said testing to produce a population of cotton plants.

Provided herein are methods of breeding cotton plants by: collecting at least one seed produced by a cotton plant grown under a stressed condition according to any of the aforementioned methods. In certain aspects, the seed is tested (e.g., genotyped and/or phenotyped) to determine the performance of, and/or a characteristic of, a parent plant and/or the offspring a plant produces.

Provided herein are cotton plants with an altered morphology. It is understood that reference to "an aspect" refers to any of the cotton plants with an altered morphology disclosed herein and should not be limited to any particular plant unless otherwise stated. In certain aspects, the cotton plant is less than about 30 inches, less than about 24 inches, less than about 18 inches, less than about 15 inches, or less than about 12 inches, and wherein the plant has at least 20 seeds, at least 30 seeds, at least 40 seeds, at least 50 seeds, or at least 60 seeds. In certain aspects, the plant is grown according any of the aforementioned methods.

Provided herein are methods of growing a population of cotton plants, wherein the cotton plants have an altered morphology, by growing under a stressed condition a population of cotton plants from cotton seeds. As stated above, it is understood that reference to "an aspect" refers to any of the methods disclosed herein and should not be limited to any particular method unless otherwise stated. In certain aspects, the stressed condition comprises growing the cotton plants of the population in an average volume per plant of growth media of less than about 2,000 mL, less than about 1,500 mL, less than about 1,000 mL, less than about 500 mL, less than about 450 mL, less than about 400 mL, less than about 300 mL, less than about 250 mL, or less than about 200 mL, for at least 40 days, for at least 50 days, for at least 60 days, for at least 70 days, for at least 75 days, or for at least 80 days during the time from the average day of germination of the cotton seeds of the population to the average day that the plants of the population produce at least one cotton boll that contains a seed, wherein the seed comprises at least one embryo with a cotyledon in the primordia stage and optionally wherein the seed comprises a black layer (restricted growth media volume). In certain aspects, the stressed condition comprises growing the population of cotton plant at a temperature of at least about 37° C., 38° C., 39° C., 40° C., 41° C., 42° C., 43° C., 44° C., 45° C., 46° C., 47° C., or 48° C. for at least about 2, 3, 4, 5, 6, 7, 8, 9, 10, 11, or 12 hours per day, for at least 40 days, for at least 50 days, for at least 60 days, for at least 70 days, for at least 75 days, or for at least 80 days during the time from the average day of germination of the cotton seeds of the population to the average day that the plants of the population produce at least one cotton boll that contains a seed, wherein the seed comprises at least one embryo with a cotyledon in the primordia stage and optionally wherein the seed comprises a black layer (high temperature). In certain aspects, the stressed condition comprises growing the population of cotton plants by providing the cotton plants of the population on average with less than about 500 mL, less than about 400 mL, less than about 300 mL, less than about 200 mL, less than about 100 mL, or less than about 50 mL of water per day on average, for at least 40 days, for at least 50 days, for at least 60 days, for at least 70 days, for at least 75 days, or for at least 80 days during the time from the average day of germination of the cotton seeds of the population germinates to the average day that the plants of the population produce at least one cotton boll that contains a seed, wherein the seed comprises at least one embryo with a cotyledon in the primordia stage and optionally wherein the seed comprises a black layer (restricted irrigation). In certain aspects, the stressed condition can be a combination of any of these.

In certain aspects, at least about 50%, 60%, 70%, 80%, 90%, or 95% of the plants in the population produce seed. In certain aspects, at least one cotton plant of the population, having produced at least one cotton boll that contains a seed, wherein the seed comprises at least one embryo with a cotyledon in the primordia stage and optionally wherein the seed comprises a black layer, is of a diminished size, such as decreased in height and/or having reduced biomass, compared to a control plant. In certain aspects, at least about 50%, 60%, 70%, 80%, 90%, or 95% of the plants in the population, having produced at least one cotton boll that contains a seed, wherein the seed comprises at least one embryo with a cotyledon in the primordia stage and optionally wherein the seed comprises a black layer, are of a diminished size, such as decreased in height and/or having reduced biomass, compared to a control plant.

In certain aspects, the population is grown in a controlled environment.

In certain aspects, at least about 50%, 60%, 70%, 80%, 90%, 95%, 98%, or 99% of the plants in the population have produced at least one cotton boll that contains a seed, wherein the seed comprises at least one embryo with a cotyledon in the primordia stage and optionally wherein the seed comprises a black layer, and are less than about 30 inches tall, less than about 24 inches tall, less than about 18 inches tall, less than about 15 inches tall, or less than about 12 inches tall. In certain aspects, at least about 50%, 60%, 70%, 80%, 90%, 95%, 98%, or 99% of the plants in the population have at least 20 seeds, at least 30 seeds, at least 40 seeds, at least 50 seeds, or at least 60 seeds.

In certain aspects, at least one plant from the population of plants grown under a stressed condition is used in a breeding program. In certain aspects, the method further comprises collecting at least one seed from at least one plant from the population of plants grown under a stressed condition. In certain aspects, the method further comprises testing (e.g., genotyping and/or phenotyping) at least one collected seed or plant grown from the collected seed. In certain aspects, the method further comprises growing and/or crossing a cotton plant based on the testing.

In certain aspects, the population of cotton plants is grown at an average density of at least 10, 30, 60, 75, 100, 125, or 150 plants per square meter. In certain aspects, the population of plants comprises at least about 50 cotton plants, at least about 100 cotton plants, at least about 500 cotton plants, at least about 1,000 cotton plants, at least about 5,000 cotton plants, at least about 10,000 cotton plants, at least about 100,000 cotton plants, at least about 500,000 cotton plants, at least about 1,000,000 cotton plants. Similarly, in certain aspects, the population of plants comprises 50 or more cotton plants, 100 or more cotton plants, 500 or more cotton plants, 1,000 or more cotton plants, 5,000 or more cotton plants, 10,000 or more cotton plants, 100,000 or more cotton plants, 500,000 or more cotton plants, or 1,000,000 or more cotton plants. In certain aspects, the population of cotton plants is grown under a stressed condition at an average density of at least 10, 30, 60, 75, 100, 125, or 150 plants per square meter, for at least 40 days, for at least 50 days, for at least 60 days, for at least 70 days, or for at least 80 days during the time from the average day of germination of the cotton seeds of the population germinates to the average day that the plants of the population produce at least one cotton boll that contains a seed, wherein the seed comprises at least one embryo with a cotyledon in the primordia stage and optionally wherein the seed comprises a black layer.

Provided herein are populations of cotton plants with an altered morphology. It is understood that reference to "an aspect" refers to any of the populations of plants disclosed herein and should not be limited to any particular population unless otherwise stated. In certain aspects, the population of plants is grown at a density of at least 30, 60, 65, 75, 100, 125, or 150 plants per square meter. In certain aspects, at least about 30%, 40%, 50%, 60%, 70%, 80%, 90%, 95%, 98%, or 99% of the plants in the population have reached a stage in their life cycle when pinhead squares have formed. In certain aspects, at least about 75%, 80%, 85%, 90%, 95%, 98%, or 99% of the plants in the population produce at least one cotton boll that contains a seed, wherein the seed comprises at least one embryo with a cotyledon in the primordia stage and optionally wherein the seed comprises a black layer. In certain aspects, at least about 75%, 80%, 85%, 90%, 95%, 98%, or 99% of the plants in the population produce at least 20 seeds, at least 30 seeds, at least 40 seeds, at least 50 seeds, or at least 60 seeds. In certain aspects, at least about 75%, 80%, 85%, 90%, 95%, 98%, or 99% of the plants in the population are less than about 30 inches tall, less than about 24 inches tall, less than about 18 inches tall, less than about 15 inches tall, or less than about 12 inches tall. In certain aspects, the average height of the population is less than about 30 inches tall, less than about 24 inches tall, less than about 18 inches tall, less than about 15 inches tall, or less than about 12 inches tall. In certain aspects, the population of plants comprises at least about 50 cotton plants, at least about 100 cotton plants, at least about 500 cotton plants, at least about 1,000 cotton plants, at least about 5,000 cotton plants, at least about 10,000 cotton plants, at least about 100,000 cotton plants, at least about 500,000 cotton plants, at least about 1,000,000 cotton plants. Similarly, in certain aspects, the population of plants comprises 50 or more cotton plants, 100 or more cotton plants, 500 or more cotton plants, 1,000 or more cotton plants, 5,000 or more cotton plants, 10,000 or more cotton plants, 100,000 or more cotton plants, 500,000 or more cotton plants, or 1,000,000 or more cotton plants.

In certain aspects, the population of plants is grown according to any of the aforementioned methods. In certain aspects, the population of plants is grown in a controlled environment.

DETAILED DESCRIPTION

Figure 1:
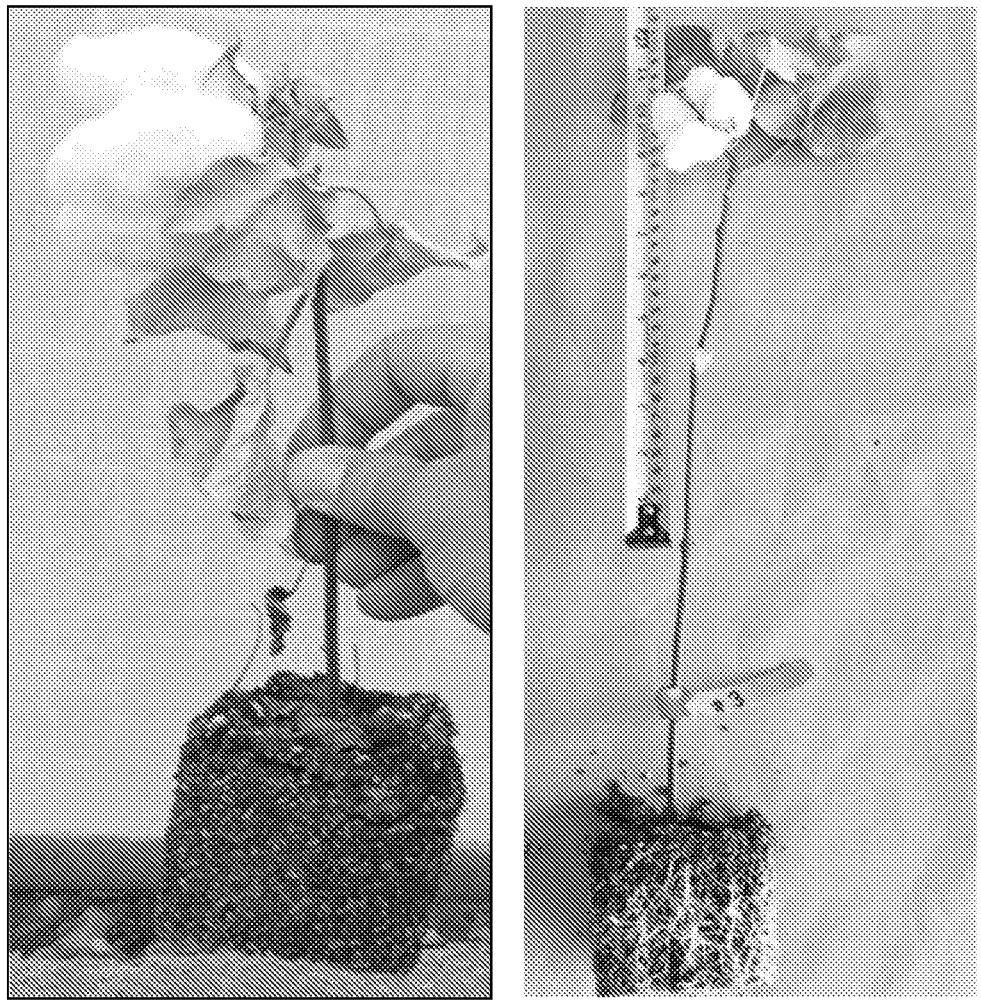
FIG. 1 shows two different cotton plants with cotton bolls (seeds) and an altered morphology. The cotton plants were grown in approximately 380 mL of soil and have a reduced stature, as evident in relationship to the hand holding it (left) and measuring tape showing 12 inches (right).
Figure 2:
FIG. 2 shows cotton plants with reduced stature in comparison to plants of normal height.
Figure 3:
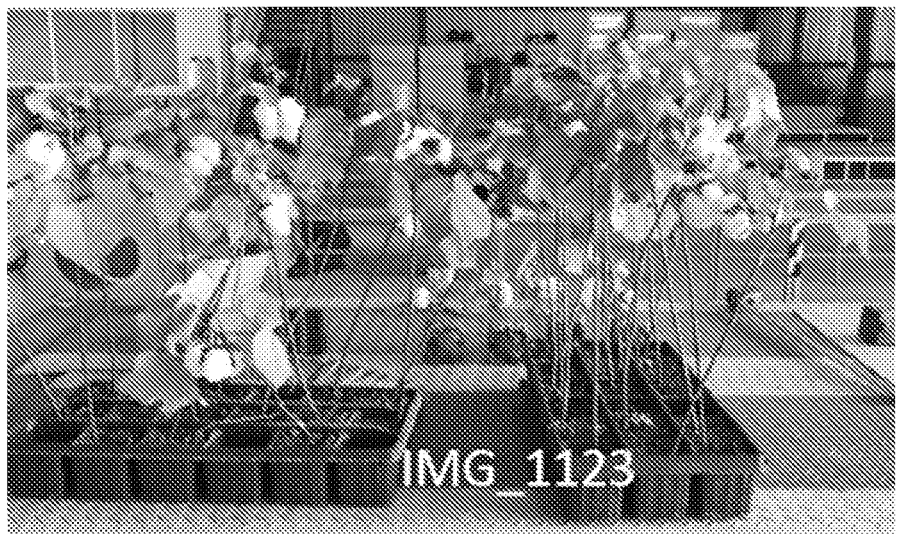
FIG. 3 shows cotton plants of reduced stature with bolls, grown at high density in a tray (top), in comparison to large, field grown plants (bottom).
Figure 3:
Figure 4:
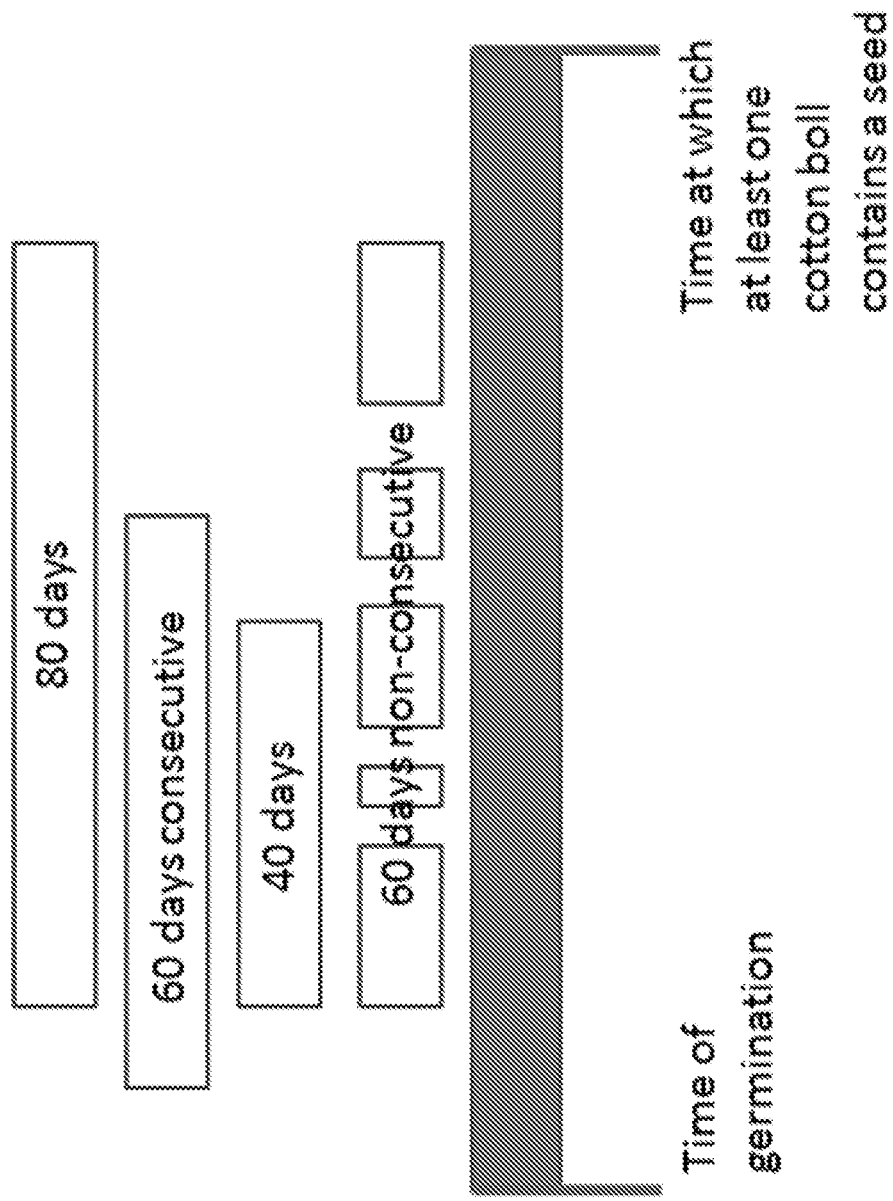
FIG. 4 illustrates examples of a time period, e.g. "at least 40 days," "at least 60 days," and "at least 80 days," during the time from when the cotton seed germinates to when the cotton plant produces at least one cotton boll that contains a seed as described in detail herein. Consecutive as well as non-consecutive days are exemplified.

Provided herein are methods of cultivating plants, such as crop plants, to produce reproductively-viable (e.g., seed-producing) plants yet with altered morphologies amendable for growth at high density and/or use in breeding programs, and in particular for growth under controlled conditions, e.g., in a controlled environment. In certain aspects, the altered morphology is a miniaturized plant such as a plant having a reduced stature, decrease in height, shortened internode length, reduced biomass, and the like. Such plants can be grown at higher densities and thus require less space for a given number of plants. This in turn makes it more feasible to grow a population of plants under cover (i.e., generally protected from pollinating insects), which in turn can increase the genetic purity of crosses achieved in a breeding program, making the breeding program more efficient and/or cost effective. Thus, in certain aspects, the methods are performed for the purpose of improving the efficiency breeding programs. Further, it has been discovered populations of plants grown under stressed conditions disclosed herein can display tighter synchronization in their development time, such as flowering and/or seed production, which also can improve the efficiency breeding programs.

Methods include subjecting plants to one or more stressed conditions and/or application of certain plant growth regulators (PRGs). Further provided are seed producing plants with altered morphologies compared to corresponding control plants.

While in certain aspects, a plant grown under the conditions of stress and/or application of a PGR disclosed herein produces seed, the number of seed need not be as many as a plant grown under normal conditions or wanted for commercial sale. For example, in a plant breeding program, only a certain number of seeds may be needed for screening and replanting, and thus any seeds in excess of that amount are unnecessary. The purpose of breeding programs is to cross plants and recover seeds from those crosses in order to capture and analyze the genetics of the seeds and/or to recover the seed so that that resulting plant and its genetics can be used in future crosses. The more efficiently that this process can be done, the more quickly new lines of plants can be developed and/or the lower the costs of development. It is currently thought that the most efficient way to grow plants in a breeding program is to grow plants in a manner that maximizes health and growth, e.g., that mimic commercial planting conditions. However, the number of seeds required for use in a breeding program may be less than the amount of seed typically produced by commercial growers attempting to maximize cotton fiber yield. In fact, producing extra seeds at certain steps of a breeding program could be considered waste. Thus, it may be acceptable at certain steps of a breeding program to grow plants that produce a fewer number of seeds than their genetic potential when grown under optimal or commercial planting conditions.

Definitions

To the extent necessary to provide descriptive support, the subject matter and/or text of the appended claims is incorporated herein by reference in their entirety.

It will be understood by all readers of this written description that the exemplary embodiments described and claimed herein may be suitably practiced in the absence of any recited feature, element or step that is, or is not, specifically disclosed herein.

It is to be noted that the term "a" or "an" entity refers to one or more of that entity; for example, "a plant," is understood to represent one or more plants. As such, the terms "a" (or "an"), "one or more," and "at least one" can be used interchangeably herein. The phrase "one or more" as used herein is interchangeable with "at least one."

Furthermore, "and/or" where used herein is to be taken as specific disclosure of each of the two specified features or components with or without the other. Thus, the term and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, technical and scientific terms used herein have the same meaning as commonly understood by one of ordinary skill in the art to which this disclosure is related. Numeric ranges are inclusive of the numbers defining the range. Even when not explicitly identified by "and any range in between," or the like, where a list of values is recited, e.g., 1, 2, 3, or 4, the disclosure specifically includes any range in between the values, e.g., 1 to 3, 1 to 4, 2 to 4, etc.

The headings provided herein are solely for ease of reference and are not limitations of the various aspects or aspects of the disclosure, which can be had by reference to the specification as a whole. Accordingly, the terms defined immediately below are more fully defined by reference to the specification in its entirety.

A used herein, a "plant" refers to a whole plant or any part thereof. For example, for purposed of this disclosure, applying a plant growth regulator to a "plant" includes applying the plant growth regulator to a whole plant or any part thereof or plant part (e.g., to the leaves, stems, roots, seeds, etc.).

As used herein, a "population of plants," "plant population," or the like refers to at least two or more plants. Most commonly, the terms relate to a breeding population of plants from which members are selected and crossed to produce progeny in a breeding program. A population of plants can include the progeny of a single breeding cross or a plurality of breeding crosses, and can be either actual plants or plant derived material, or in silico representations of the plants. The population members need not be identical to the population members selected for use in subsequent cycles of analyses or those ultimately selected to obtain final progeny plants. Often, a plant population is derived from a single biparental cross, but may also derive from two or more crosses between the same or different parents. Although a population of plants may comprise a small plurality of individuals, those of skill in the art will recognize that plant breeders commonly use population sizes ranging from one or two hundred individuals to several thousand, and that the highest performing 5-20% of a population is what is commonly selected to be used in subsequent crosses in order to improve the performance of subsequent generations of the population.

As used herein, the term "non-naturally occurring" condition, substance, composition, entity, plant, organism, individual, and/or any combination thereof, or any grammatical variants thereof, is a conditional term that explicitly excludes, but 914 excludes, those forms that are well-understood by persons of ordinary skill in the art as being "naturally-occurring," or that are, or might be at any time, determined or interpreted by a judge or an administrative or judicial body to be, "naturally-occurring."

As used herein, the terms "flower" and "inflorescence" are used interchangeably.

The methods described herein are not limited to the process by which a population of plants is brought together to be cultivated. For example, it is commonly understood that seeds form after fertilization and comprise a zygote or embryo surrounded by tissues that were once part of the ovule. However, the term "seed" as used herein can also have a more general meaning to include any viable plant cell capable of undergoing cell division (e.g. mitosis) to grow, and/or develop, and, in certain embodiments, form reproductive structures. A seed can also be anything that can be sown, or planted, directly into growth media including vegetative structures, like potato tubers ("seed" potatoes), and/or sugarcane stalks, and/or cells of a callus. A seed may also comprise a zygote or embryo encased in some form of protective layer. In certain embodiments the protective layer comprises tissues derived from plant cells (e.g. cells of the maternal parent ovule), and a seed may or may not include other tissues, for example, when the layers of the seed protecting or enclosing the embryo are technically considered to be part of a dried fruit or kernel, as they are in corn and sunflower. Even artificial methods of coating or protecting an embryo with a wide range of chemicals that serve at least the purpose of protecting and/or sustaining, and or otherwise supporting the embryo are envisioned. A seed could even be a naked embryo, provided one was able to culture it into a vegetative or flowing plant using one or more of the methods described herein. One of skill will immediately appreciate that the methods disclosed herein could be used in conjunction with any other process that brings about a population of plants growing in a controlled environment in the high densities and/or in at least one of the stressed conditions described herein.

As used herein, the term "elite," "elite plant," and the like describes a group, germplasm, or population of at least one crop plant that has resulted from human-directed breeding and selection for superior agronomic performance. An "elite population" is an assortment of elite individuals or lines that can be used to represent the state of the art in terms of agronomically superior genotypes of a given crop species, such as cotton. Similarly, an "elite germplasm" or "elite strain of germplasm" is an agronomically superior germplasm, typically derived from and/or capable of giving rise to a plant with superior agronomic performance, such as an existing or newly developed elite line of cotton. In contrast, an "exotic plant," "exotic line," or "exotic germplasm" is a plant, line, or germplasm derived from a plant not belonging to an available elite line or strain of germplasm. In the context of a cross between two plants or lines of germplasm, an exotic germplasm is not closely related by descent to the elite germplasm with which it is crossed. Most commonly, the exotic germplasm is not derived from any known elite line of a crop, but rather is selected to introduce genetic elements (typically desired alleles) into a breeding program.

As used herein, a "control" plant is a plant (or a member of a population of plants) recognized as having a representative phenotype (e.g., number of inflorescences, number of seeds, height, internode length, biomass, and the like), of a plant grown under normally recommended growing conditions, but that is in other respects, such as genetic makeup, comparable to a plant grown under a stressed condition. For example, one of ordinary skill in the art would understand a control plant to have one or more of the following attributes: results from a seed derived from the same haploid induction cross; has at least one parent in common with the treated plant; shares a common ancestor with the treated plant within twelve generations; shares sufficient common genetic heritage with the treated plant that one of ordinary skill in the art of plant breeding would recognize the control plant as a valid comparison for establishing a correlation between the stressed growth condition and the resulting phenotype; and/or achieves a morphology considered typical of the mature plant. One of ordinary skill in the art will recognize that a control plant that by chance (e.g., a statistical outlier), by some other type of manipulation, or other reason comprises a phenotype that varies from a representative phenotype of control plants would not be an appropriate control plant for comparison.

As used herein, the term "grown in a controlled environment," means that a plant or population of plants is grown in an enclosure capable of excluding pollinating insects. Such enclosures include screened in enclosures such as cages, green houses, hothouses, grow houses, hoop houses, warehouses, and growth chambers. It is understood that "capable of excluding pollinating insects," does not mean that all pollinating insects are absolutely excluded, but that fewer pollinating insects have access to the plant or population of plants than if the plant or population of plants was not grown in a controlled environment. Growth in a controlled environment may also include control over one or more additional factors such as lighting, temperature, humidity, irrigation, growth media volume, protection from the elements such as wind and hail, exclusion of windborne pollen, and protection from windblown pesticide contamination.

A plant "growth media" as referred to herein can be any type of substance suitable for growing plants. Commonly, soil is used as a growth media for growing plants.

A flower bud of a cotton plant can be referred to as a "square". It generally comprises a central corolla containing re-productive structures (e.g. anthers) and sepals and surrounded by three (or sometimes four) bracts. Several morphological stages of square development (i.e. "squaring") are recognized by cotton growers. The "pinhead" square stage begins when the square first becomes identifiable to the naked eye and it is followed by the "match-head" or "one-third grown" square. Later, the bud takes on a candle shape, typically just before blooming.

Stressed Conditions

Disclosed herein are methods including growing plants, producing seeds, and conducting plant breeding, and the like, in which certain stresses are applied to the plants. These stressed conditions deviate from the established conditions recommended for commercial production or conditions that would likely be tested in research programs aimed at optimizing growth conditions for maximum plant health and yield. In certain aspects, one or more of these stressed conditions is the result of human control and/or manipulation of the growing conditions ("controlled conditions," e.g., in a "controlled environment") and vary from conditions that may naturally be experienced by plants grown in the field. That is, even though plants in the field may experience conditions of e.g., drought and/or high temperatures due to natural weather conditions, certain aspects of the methods disclosed herein are distinguishable from those conditions because the conditions are being controlled and/or manipulated by humans, such as within an enclosure or by planting in a restricted amount of growth medium and/or growing plants to maturity at high density.

In certain aspects, a method involves growing a plant from a seed. In certain aspects, application of one or more stressed conditions results in an altered plant morphology compared to a control plant. In certain aspects, one or more of these stressed conditions can be applied from when the seed is sown and/or germinated and maintained throughout all or a portion of the period during which a plant is grown. Further in certain aspects, a plant with an altered morphology and despite the stressed conditions, still produces at least some seed that can be used, for example, in a breeding program.

While the details of different stressed conditions are described separately below, it is understood that methods herein can comprise any one, any combination of, or all of the stressed conditions. Further, while the stressed conditions may be described as applied to a plant, it is understood that any of such stressed condition or combination of stressed conditions can be applied to a population of plants.

Restricted Growth Media Volume

In certain aspects, the stressed condition applied to a plant is growing the plant in a restricted volume of growth media that is reduced, in some instances significantly from the generally recommended amount, to achieve altered plant morphologies. In certain aspects, plants grown under restricted soil volume stress (or a combination of soil volume stress with other types of stressed conditions and/or the application of plant growth regulators) resulting in altered morphologies still produce at least some seed.

Cotton plants, for example, are commonly grown spaced apart in open fields or if in containers, in containers with at least about 3 L of soil volume, e.g., 3 L buckets or bags, to allow them what is generally considered sufficient room for healthy growth. In contrast, in certain aspects of the methods herein, a restricted soil volume is less than about 2,000 mL, less than about 1,500 mL, less than about 1,000 mL, less than about 900 mL, less than about 800 mL, less than about 700 mL, less than about 600 mL, less than about 500 ml, less than about 450 mL, less than about 400 mL, less than about 350 mL, less than about 300 mL, less than about 250 mL, or less than about 200 mL of soil volume. In certain aspects, a restricted soil volume is from any of about 100 mL, 200 mL, 300 mL, 400 mL, 450 mL, 500 mL, or 1,000 mL of soil volume to any of about 300 mL, 400 mL, 450 mL, 500 mL, 600 mL, 700 mL, 800 mL, 900 mL, 1,000 mL, 1,500 mL, or 2,000 mL of soil volume. For example, from about 200 mL to about 500 mL, from about 250 mL to about 450 mL, from about 300 mL to about 500 mL, or from about 350 mL to about 450 mL of soil volume.

It is understood that the amount of soil that a plant is grown in can be restricted by growing the plant in a container. In certain aspects, one plant is grown per container. More than one plant, however, can be grown in a shared container. In such cases, the amount of soil volume per plant can be considered the amount of soil volume in the container divided by the number of plants in the container.

It may be common practice to sow a seed in a small volume of soil and then replant the plant into a larger container containing more soil, or even a series of successively larger containers, as the plant grows and becomes larger. If the plant is replanted as it grows into an amount of soil that does not create stress, it will not achieve the morphologies described herein. In contrast, in the methods disclosed herein, a plant is grown in a restricted soil volume for a defined period of time so that the plant is stressed as it grows. In certain aspects, a cotton plant is grown in a restricted soil volume for at least 40 days, at least 50 days, at least 60 days, at least 70 days, at least 75 days, at least 80 days, or at least 85 days during the time from when the seed germinates to when the plant produces at least one cotton boll that contains a seed, wherein the cotton seed comprises at least one embryo with a cotyledon in the primordia stage. In certain aspects, the cotton seed comprises a black layer. Under permissive conditions for germination, a cotton seed, for example, will germinate generally around 12 hours to 48 hours after being sown. Similarly, in certain aspects, a non-cotton plant is grown in a restricted soil volume for a corresponding percentage of days during the time from when the seed germinates until when the plant reaches its reproductive stage. The number of days during which the plant is grown under the stressed condition need not be consecutive, i.e., the number of days in the restricted soil volume is the cumulative number of days from when the seed is sown or germinates to when the plant reaches reproductive stage. In certain aspects, the period of time is in consecutive days.

Cultivation at High Temperatures

In certain aspects, plants are stressed by cultivation at high temperatures. Without being bound by theory, it is suggested in the art that temperatures above about 35° C. can hamper photosynthesis and additionally, plant development and survival. In certain aspects, cultivation at high temperatures is combined with the aforementioned methods of growing plants in restricted soil volumes and/or with the below mentioned methods of growing plants with restricted irrigation. In certain aspects, the temperatures are at least about 5° C. higher than what would normally be recommended as the highest temperature at which to grow the plant.

It has been discovered that growing a plant at daily high temperatures in the range of about 37° C. to about 48° C., even for just a few hours a day, can result in altered plant morphologies. In certain aspects, plants that are grown under high temperature stress (or a combination of high water stress with other types of stressed conditions and/or the application of plant growth regulators) resulting in altered morphologies still produce at least some seed.

In certain aspects, a plant is grown at a temperature of at least about 37° C., 38° C., 39° C., 40° C., 41° C., 42° C., 43° C., 44° C., 45° C., 46° C., 47° C., or 48° C. In certain aspects, the duration of time per day during which a plant is grown at the temperature can be as little as 2 hours, or at least about 2 hours, 3 hours, 4 hours, 5 hours, 6 hours, 7 hours, 8 hours, 9 hours, 10 hours, 11 hours, or 12 hours per day. The duration of time per day during which a plant is exposed to the above temperatures can be consecutive and/or cumulative over the course of a day, including non-daylight hours. Generally, however, the temperature rises during the day and then decreases overnight. In certain aspects, plants are grown at cooler temperatures overnight, such as at least 5° C., 10° C., 15° C., 20° C., or 25° C. cooler than the maximum daytime temperature. In certain aspects, the average nighttime temperature is from about 18° C. to about 22° C. In certain aspects, a cotton plant is grown at these high temperatures and times for at least 40 days, at least 50 days, at least 60 days, at least 70 days, at least 75 days, at least 80 days, or at least 85 days during the time from when the seed germinates to when the plant produces at least one cotton boll that contains a seed, wherein the cotton seed comprises at least one embryo with a cotyledon in the primordia stage. In certain aspects, the cotton seed comprises a black layer. Similarly, in certain aspects, a non-cotton plant is grown at these high temperatures and times for a corresponding percentage of days during the time from when the seed germinates until when the plant reaches its reproductive stage. The number of days during which the plant is grown under the stressed condition need not be consecutive, i.e., the number of days the plant is grown at a high temperature is the cumulative number of days from when the seed is sown or germinates to when the plant reaches reproductive stage. For example, a plant can be grown at a high temperature for a few days, then at a lower temperature for a day or more, and then back to being grown at a high temperature, and so forth. In certain aspects, the period of time is in consecutive days.

In certain aspects, the duration of time that a plant is subjected to high heat is limited to prevent overstressing the plant to a point that it will not produce seeds. Thus, in certain aspects, on at least about 50%, 60%, 70%, 80%, 90%, 95%, 98%, or 100% of the days on which the plant is grown at a temperature of at least about 37° C., 38° C., 39° C., 40° C., 41° C., 42° C., 43° C., 44° C., or 45° C., it is not grown at this temperature for more than about 6, 7, 8, 9, 10, 11, 12, 13, 14, 15, or 16, 18, or 20 hours per day, i.e., grown below this temperature for at least 4, 6, 8, 9, 10, 11, 12, 13, 14, 15, 16, 17, or 18 hours per day. In certain aspects, on at least about 50%, 60%, 70%, 80%, 90%, 95%, 98%, or 100% of the days on which the plant is grown at a temperature of at least about 37° C., 38° C., 39° C., 40° C., 41° C., 42° C., 43° C., 44° C., or 45° C., the plant is also grown at a temperature of about 18° C. to 22° C. for at least 2, 3, 4, 5, 6, 7, 8, 9, 10, 11, 12, 13, 14, 15, or 16 hours per a day.

A combination of stressed conditions may produce an additive effect in which the severity of an individual stressed condition may be reduced but still achieve a plant with a desired altered morphology. In certain aspects, when a plant is grown under restricted growth media volume and/or restricted irrigation stressed conditions as described elsewhere herein, the high temperature stressed condition can be reduced to at least about 32° C., 33° C., 34° C., 35° C., or 36° C., under the conditions of hours per day, days between germination and seed formation, etc., otherwise described herein.

As described anywhere herein unless otherwise stated, while the days between germination and seed formation, reaching reproductive stage, and the like during which various stressed conditions are applied will generally overlap, it is not necessary that they correspond or even overlap. For example, a plant could be subjected to limited irrigation on one day at a normal temperature and then given a normal amount of water the next day but subjected to high temperatures. For example, a plant may be grown in a restricted soil volume for a period of time under normal water and temperature conditions, and then replanted in a normal soil volume but subjected to temperature and/or irrigation stress.

Restricted Irrigation

In certain aspects, plants are stressed by restricting the amount of water that they receive. In certain aspects, water restriction is combined with the aforementioned methods of growing plants in restricted soil volumes and/or high temperatures. For example, whereas generally recommended irrigation of a plant may be about 500 mL to about 1,000 mL of water per 24 hour period for most growing days, in certain aspects, a plant is provided with about $1/10^{th}$ or less water, such as less than about 100 mL of water, during the same period of time. In certain aspects, plants are grown under water restriction (or a combination of restricted irrigation stress with other types of stressed conditions and/or the application of plant growth regulators) resulting in altered morphologies still produce at least some seed.

In certain aspects, the amount of restricted water is not determined as a daily basis, but rather the average amount of water per day over a given number of days. For example, a plant that is watered with 600 mL on a first day and then not watered the next two consecutive days would on average have been water with 200 mL of water per day during the three day period.

In certain aspects, a plant is provided with less than about 500 mL, less than about 400 mL, less than about 300 mL, less than about 200 mL, less than about 100 mL, or less than about 50 mL of water per day on average. In certain aspects, a plant is provide with any of about 1 mL, 10 mL, 25 mL, 50 mL, 100 mL, 200 mL, 250 mL, or 300 mL of water per day on average, to any of about 50 mL, 100 mL, 200 mL, 250 mL, 300 mL, 400 mL, or 500 mL of water per day on average. In certain aspects, a cotton plant is grown under any of these restricted irrigation conditions for at least 40 days, at least 50 days, at least 60 days, at least 70 days, at least 75 days, at least 80 days, or at least 85 days during the time from when the seed germinates to when the plant produces at least one cotton boll that contains a seed, wherein the cotton seed comprises at least one embryo with a cotyledon in the primordia stage. In certain aspects, the cotton seed comprises a black layer. Similarly, in certain aspects, a non-cotton plant is grown under restricted irrigation conditions for a corresponding percentage of days during the time from when the seed germinates until when the plant reaches its reproductive stage.

Plant Growth Regulators (PGRs)

Certain aspects provide for the use of plant growth regulators (PGRs) to induce altered plant morphologies, either by the use of PGRs alone or in combination with one or more of the aforementioned stressed conditions to achieve an altered morphology. In certain aspects, plants treated with a PGR (or a combination of PGR with one or more aforementioned stresses) resulting in altered morphologies still produce at least some seed.

In certain aspects provided herein, a plant can be contacted with a wide variety of PGRs. PGRs are a class of compounds that affect the cellular processes, growth, development or behavior of a plant. PGR can be responsible for accelerating or retarding the rate of growth or maturation or otherwise altering the behavior of a plant. In some aspects, a PGR is a naturally-occurring plant hormone capable of altering flower development, internode length, apical dominance, ripening, root architecture, fruiting and/or other characteristics of a plant. In some aspects, a PGR is a chemical capable of altering flower development, internode length, apical dominance, ripening, root architecture, fruiting and/or other characteristics of a plant. Plant growth regulators include auxins (e.g. IAA) and auxin inhibitors, cytokinins (e.g. BAP) and cytokinin inhibitors, compounds that can stimulate ethylene production (i.e. ACC and the like) and compounds that can inhibit ethylene production (AVG and the like), and compounds that inhibit ethylene perception (silver and the like). Plant growth regulators also comprise compounds that modulate plant perception, signaling, and/or behavior, such as giberrellins and their inhibitors (e.g. Paclobutrazol (PBZ) or uniconazole), abscisic acid and its inhibitors, and jasmonic acid and its inhibitors. In certain aspects, the plant growth regulator is a plant hormone, gibberellic acid inhibitor, cytokinin, or any combination thereof.

In certain aspects, a PGR is an exogenously-provided compound that can be introduced to the surface of a plant and migrate into a plant tissue. In some aspects, the PGR acts extracellularly within the plant tissue, such as interacting with receptors on the outer cell surface. In some aspects, the PGR enters into cells within the tissue. In some aspects, the PGR is contained within a liquid. Such liquids include, but are not limited to aqueous and non-aqueous solutions, suspensions, emulsions, and colloidal dispersions. A "plant treatment solution" or "treatment solution" can refer to any solution of liquid that comprises a PGR.

In certain aspects, contact between the plant and the treatment agent is achieved by dipping, submerging, or otherwise inserting the plant into a reservoir of liquid comprising the plant treatment agent. Other methods of contacting a plant with a treatment agent include spraying or misting the plant with a solution comprising a plant treatment agent or agitating or tumbling a plant in a solution comprising a plant treatment agent. In certain aspects, contact between the plant and the treatment agent is achieved by a soil drench, which comprises adding a liquid treatment agent to the soil or growth medium near the plant roots.

In certain aspects, liquids are of an aqueous nature. In certain aspects, aqueous liquids can comprise water soluble components. In certain aspects, aqueous liquids can comprise water insoluble components, can comprise an insoluble component that is made soluble in water by addition of a surfactant, or can comprise any combination of soluble components, insoluble components, and surfactants.

In certain aspects, the PGR can be any compound known to inhibit the synthesis, uptake, or persistence of gibberellic acid in a plant. For example, one non-limiting example of a PGR that can be used with this invention is selected from the group comprising chlormequat-CL, mepiquat-CL, AMO-1618, clorphonium-Cl, tetcylacis, ancymidol, flurprimidol, paclobutrazol, uniconazole-P, inabenfide, prohexadione-CA, trinexapac-ethyl, daminozide, exo-16,17-, and dihydro-GA5-13-acetate. Other examples include peptide hormones, for example, systemin, phytosulfokine, rapid alkalinization factor. In certain aspects, the PGR is mepiquat chloride.

IAA is indole-3-acetic acid, and IBA is inodole-3-butyric acid. Both are naturally-occurring forms of a class of plant hormones called auxins. Other variations of auxin can be used, including synthetic auxins, such as 2,4-D (2,4-Dichlorophenoxyactic acid and □-NAA (□-Naphthalene acetic acid).

As used herein, PBZ is paclobutrazol, (2S,3S)-1-(4-chlorophenyl)-4,4-dimethyl-2-(1,2,4-triazol-1-yl) pentan-3-ol, also written as C15H10ClN3O, a plant growth regulator and triazole fungicide. It is a known antagonist of the plant hormone gibberellins that inhibits giberellin biosynthesis, reducing internodal growth and increasing stem girth. BAP is 6-Benzylaminopurine, N-(Phenylmethyl)-7H-pruin-6-amine, also written as C12H11N5. IAA is indole-3-acetic acid, and IBA is inodole-3-butyric acid. Both are naturally-occurring forms of a class of plant hormones called auxins. Other variations of auxin can be used with this invention, including synthetic auxins, such as 2,4-D (2,4-Dichlorophenoxyactic acid) and 1-NAA (1-Naphthalene acetic acid).

As used herein, uniconazole is (e)-(+/−)-beta-((4-chlorophenyl)methylene)-alpha-(1,1-dimethylethyl)-1h-1,2,4-triazole-1-ethanol, also written as C15H18ClN3O, also known as uniconazole-P. It is a triazole-type plant growth retardant and known antagonist of the plant hormone giberellin that reduces internodal growth and increases stem girth.

As used herein, mepiquat chloride is also known as N,N-dimethylpiperidinium chloride, C7H16ClN, PIX®, mepiquat-CL.

In general, PGRs used herein will be water soluble agents. However, the use of PGRs with high, intermediate, low or negligible water solubility can, in certain aspects, be facilitated by the use of liquid compositions that also comprise various transfer or conditioning agents. Transfer or conditioning agents can comprise any agent that facilitates migration of plant treatment agents to the plant (e.g., plant cells) and/or that facilitate uptake of plant treatment agents by the plant. Transfer or conditioning agents include, but are not limited to, (a) surfactants, (b) an organic solvents or an aqueous solutions or aqueous mixtures of organic solvents, (c) oxidizing agents, (d) acids, (e) bases, (f) oils, (g) enzymes, or combinations thereof. In certain aspects, methods can optionally include an incubation step, a neutralization step (e. g., to neutralize an acid, base, or oxidizing agent, or to inactivate an enzyme), a rinsing step, or combinations thereof whereby the liquid and plant treatment agent contained therein is treated either before or after delivery to the plant. Transfer or conditioning agents thus include, but are not limited to, emulsions, reverse emulsions, liposomes, and other micellar-like compositions. Examples of useful adjuvants include surfactants and effective molecules contained therein, which include sodium or lithium salts of fatty acids (such as tallow or tallowamines or phospholipids). Transfer or conditioning agents can comprise salts including, but not limited to, sodium, ammonium, calcium, lithium, magnesium, chloride, sulfide, and sulfate salts. Certain aspects of the methods provided herein use counter-ions or other molecules that are known to associate with plant treatment agents. For certain negatively charged plant treatment agents such as polynucleotides, cations such as inorganic ammonium ions, alkyl ammonium ions, lithium ions, polyamines such as spermine, spermidine, or putrescine, and the like can be used. Organic solvents useful in conditioning a plant cell to permeation with certain plant treatment agents including, but not limited to polynucleotides, are solvents such as DMSO, DMF, pyridine, N-pyrrolidine, hexamethylphosphoramide, acetonitrile, dioxane, polypropylene glycol, or other solvents that are miscible with water. Naturally derived or synthetic oils with or without surfactants or emulsifiers can be used, e. g., plant-sourced oils, crop oils (such as those listed in the 9th Compendium of Herbicide Adjuvants, publicly available on the world wide web (internet) at "herbicide.adjuvants.com") can be used. Oils useful in certain liquid compositions used in the methods provided herein include, but are not limited to, paraffinic oils, polyol fatty acid esters, or oils with short-chain molecules modified with amides or polyamines such as polyethyleneimine or N-pyrrolidine.

In certain aspects of any of the methods herein, a plant is contacted with the PGR by drenching, gassing, injecting, or spraying.

In certain aspects, a broad range of chemical concentrations can be used in conjunction with these methods and one of ordinary skill in the art can optimize the dose administered to a given plant subjected to any of the stressed conditions disclosed herein in order to maximize a desired morphology.

In certain aspects, the use of the PGR is inconsistent with prior methods of applying the PGR. For example, it is expressly recommended by the manufacturer that a user should not apply mepiquat chloride until after pinhead squares have formed on the plant (typically 25-30 days after planting (DAP)). In certain aspects, however, the method comprises applying the PGR before the first pinhead square stage. In certain aspects, the method comprises applying the PGR at a day not past 20 days, 21 days, 22 days, 23 days, or 25 days after germination. In certain aspects, the method comprises applying a PGR at 20 to 25 days after germination, 20 to 24 days after germination, 21 to 23 days after germination, or 22 to 24 days after germination.

Altered Plant Morphologies

Provided herein are plants with altered morphologies due to the application of one or more stressed conditions and/or application of a PGR while the plant is growing. That is, a plant with an altered morphology disclosed herein grown according to any of the aforementioned methods. In particular, the aforementioned growing conditions result in plants that typically have a reduced height, shorter internode lengths, and/or decreased biomass than plants grown under normal or recommended growing conditions. While the growth of these plants may appear sickly or stunted to one of ordinary skill in the art, it has been discovered that under the right conditions, such plants can produce at least some seeds and thus can be useful, for example, in plant breeding programs. In certain aspects, a plant is grown in a controlled environment, for example, to protect it pollinating insects.

In certain aspects, the height of a cotton plant is measured from the cotyledon to the topmost structure of the plant. As used herein for a cotton plant, measuring to the topmost structure of the cotton plant (also referred to herein as "top of the plant") means measuring to the uppermost node that is associated with an unfurled leaf at least 1 inch in diameter. One of ordinary skill in the art would recognize that there can be younger leaves higher up, but that they are curled, and thus it is standard to ignore them when measuring plant height in order ensure consistent measurements.

On of ordinary skill in the art will recognize that measuring from the cotyledon nodes is more consistent, but the height of a plant can also be measured from the top of the soil where the plant is growing to the topmost structure of the plant as defined above. Without manipulation of the soil level intended to obtain a pre-desired result, which is excluded from a height measurement of this disclosure, one of ordinary skill in the art would understand that the distance between the top of the soil and the cotyledon nodes is about 2 to 6 inches (e.g., approximately 4 inches on average). Thus, one of ordinary skill in the art would understand that if a measurement of plant height is taken from the top of the soil to the top of the plant, that height can be converted for comparison purposes to the heights disclosed herein by subtracting 4 inches, i.e., that average distance between the top of the soil and the cotyledon nodes. For example, if a plant is measured from the top of the soil to the top of the plant and the height is recorded as 26 inches, for purposes of this disclosure, that plant's height is considered 22 inches.

In certain aspects, a plant is a plant having produced seed but being less than about 30 inches tall, less than about 24 inches tall, less than about 18 inches tall, less than about 15 inches tall, or less than about 12 inches tall. In certain aspects, a plant is a plant having produced seed but being from any of about 6 inches tall, 12 inches tall, 15 inches tall, 18 inches tall, or 24 inches tall to any of about 12 inches tall, 15 inches tall, 18 inches tall, 24 inches tall, or 30 inches tall (one of ordinary skill in the art would understand how to convert inches into other units such as centimeters or meters). While it is understood that a plant growing from a seed will start out, for example, less than 12 inches tall, the growing plant during its vegetative stage will not have produced seeds. By the time that a plant grown under normal growth conditions reaches it reproductive stage and produces seed, it will be taller than, for example, 12 inches tall.

In certain aspects, the plant is a cotton plant having produced at least one cotton boll that contains a seed, wherein the seed comprises at least one embryo with a cotyledon in the primordia stage, but being less than about 30 inches tall, less than about 24 inches tall, less than about 18 inches tall, less than about 15 inches tall, or less than about 12 inches tall. In certain aspects, the plant is a cotton plant having produced at least one cotton boll that contains a seed, wherein the seed comprises at least one embryo with a cotyledon in the primordia stage, but being from any of about 6 inches tall, 12 inches tall, 15 inches tall, 18 inches tall, or 24 inches tall to any of about 12 inches tall, 15 inches tall, 18 inches tall, 24 inches tall, or 30 inches tall. While it is understood that a cotton plant growing from a seed will start out, for example, less than 12 inches tall, the growing cotton plant during its vegetative stage will not have produced seeds. By the time that a cotton plant grown under normal growth conditions produces at least one cotton boll that contains a seed, it will be taller than, for example, 12 inches tall.

In certain aspects, a plant is less than about 30 inches tall, less than about 24 inches tall, less than about 18 inches tall, less than about 15 inches tall, or less than about 12 inches tall but has at least 20 seeds, at least 30 seeds, at least 40 seeds, at least 50 seeds, or at least 60 seeds.

In certain aspects, the plant is a cotton plant that is less than about 30 inches tall, less than about 24 inches tall, less than about 18 inches tall, less than about 15 inches tall, or less than about 12 inches tall but has at least 20 seeds, at least 30 seeds, at least 40 seeds, at least 50 seeds, or at least 60 seeds.

Certain aspects provide for growing a population of plants comprising plants with an altered morphology, wherein the plants in the population are grown according to the any of the methods disclosed herein. In certain aspects, at least about 50%, 60%, 70%, 80%, 90%, 95%, 98%, or 99% of the plants in the population produce seed. In certain aspects, at least one plant of the population is of a reduced height compared to a control plant. In certain aspects, at least about 50%, 60%, 70%, 80%, 90%, 95%, 98%, or 99% of the plants in the population are of a reduced height compared to a control plant. In certain aspects, the population is grown in a controlled environment. In certain aspects, at least about 50%, 60%, 70%, 80%, 90%, or 95% of the plants in the population are less than about 30 inches tall, less than about 24 inches tall, less than about 18 inches tall, less than about 15 inches tall, or less than about 12 inches tall. In certain aspects, at least about 50%, 60%, 70%, 80%, 90%, or 95% of the plants in the population are from any of about 6 inches tall, 12 inches tall, 15 inches tall, 18 inches tall, or 24 inches tall to any of about 12 inches tall, 15 inches tall, 18 inches tall, 24 inches tall, or 30 inches tall. In certain aspects, the average height of a plant in the population is less than about 30 inches tall, less than about 24 inches tall, less than about 18 inches tall, less than about 15 inches tall, or less than about 12 inches tall. In certain aspects, the average height of a plant in the population is from any of about 6 inches tall, 12 inches tall, 15 inches tall, 18 inches tall, or 24 inches tall to any of about 12 inches tall, 15 inches tall, 18 inches tall, 24 inches tall, or 30 inches tall. In certain aspects, at least about 50%, 60%, 70%, 80%, 90%, 95%, 98%, or 99% of the plants in the population have at least 20 seeds, at least 30 seeds, at least 40 seeds, at least 50 seeds, or at least 60 seeds. In certain aspects, the plant is a cotton plant and at least about 50%, 60%, 70%, 80%, 90%, 95%, 98%, or 99% of the plants in the population have reached a stage in their life cycle wherein pinhead squares have formed.

In certain aspects, the population of plants is grown at an average density of at least 10 plants per square meter. In certain aspects, the population of plants is grown at an average density of at least 30 plants per square meter. In certain aspects, the population of plants is grown at an average density of at least about 60 plants per square meter. In certain aspects, the population of plants is grown at an average density of at least 67 plants per square meter. In certain aspects, the population of plants is grown at an average density of at least 75 plants per square meter. In certain aspects, the population of plants is grown at an average density of at least 100 plants per square meter. In certain aspects, the population of plants is grown at an average density of at least 125 plants per square meter. In certain aspects, the population of plants is grown at an average density of at least 150 plants per square meter. In certain aspects, the population of plants is grown at an average density of about 10, 30, 60, 75, 100, 125, or 150 plants per square meter or any range in between.

In certain aspects, the population of plants comprises at least about 50 cotton plants, at least about 100 cotton plants, at least about 500 cotton plants, at least about 1,000 cotton plants, at least about 5,000 cotton plants, at least about 10,000 cotton plants, at least about 100,000 cotton plants, at least about 500,000 cotton plants, at least about 1,000,000 cotton plants. Similarly, in certain aspects, the population of plants comprises 50 or more cotton plants, 100 or more cotton plants, 500 or more cotton plants, 1,000 or more cotton plants, 5,000 or more cotton plants, 10,000 or more cotton plants, 100,000 or more cotton plants, 500,000 or more cotton plants, or 1,000,000 or more cotton plants.

Certain aspects provide for a cotton plant grown under any of the stressed conditions disclosed herein, and grown as a member of a population of cotton plants, wherein the cotton plant is grown in the population with an average density of at least 10, 30, 60, 67, 75, 100, 125, or 150 plants per square meter, for at for at least 40 days, for at least 50 days, for at least 60 days, for at least 70 days, or for at least 80 days during the time from when the cotton seed germinates to when the cotton plant produces at least one cotton boll that contains a seed, wherein the seed comprises at least one embryo with a cotyledon in the primordia stage.

Plant Breeding

In addition to growing a plant, such as to produce a plant with an altered morphology and/or produce a seed, methods provided herein also apply the methods of growing a plant for breeding purposes. In certain aspects, at least one seed is collected from a plant grown by at least one of the aforementioned methods and/or having one of the aforementioned morphologies. In certain aspects, the collected seed or plant grown from the seed can be tested (also referred to as "screened") for traits. In certain aspects, the seed is tested by genotyping and/or phenotyping. In certain aspects, the information obtained by testing is used as the basis for growing and/or crossing a plant or otherwise used in a plant breeding program.

Commercial plants, such as cotton, are generally grown in open fields because the space needed to grow large populations of plants. One advantage of growing plants with an altered morphology, in particular plants with reduced height compared to control plants, is that shorter plants tend to also be more compact overall, i.e., they take up less space. This attribute—as well as the potential of using a reduced amount of soil volume per plant-allows plants to be grown at higher densities than recommended or considered viable to produce plants capable of seed production. Under normal planting densities, a population of 1000 cotton plants requires about 40,000 square meters of space. Using the methods described herein that reduce the size of the plants, the same size population can be grown with only about 4,800 square meters of space. This makes it much more feasible to grow large populations of plants in controlled environments, such as to exclude pollinating insect that may interfere with crosses made for plant breeding. In certain aspects, a plant is grown as part of a population of plants where the average density of plants is at least 10 plants per square meter. In certain aspects, a plant is grown as part of a population of plants where the average density of plants is at least 30 plants per square meter. In certain aspects, a plant is grown as part of a population of plants where the average density of plants is at least 60 plants per square meter. In certain aspects, a plant is grown as part of a population of plants where the average density of plants is at least 67 plants per square meter. In certain aspects, a plant is grown as part of a population of plants where the average density of plants is at least 75 plants per square meter. In certain aspects, a plant is grown as part of a population of plants where the average density of plants is at least 100 plants per square meter. In certain aspects, a plant is grown as part of a population of plants where the average density of plants is at least 125 plants per square meter. In certain aspects, a plant is grown as part of a population of plants where the average density of plants is at least 150 plants per square meter. In certain aspects, a plant is grown as part of a population of plants where the average density is about 10, 30, 60, 75, 100, 125, or 150 plants per square meter or any range in between. Certain aspects provide for such a population of plants wherein the population comprises plants with an altered morphology and/or grown according to the methods provided herein.

A population of plants with an average density disclosed anywhere herein may be relatively small to very large. In certain aspects, the population of plants comprises at least about 50 cotton plants, at least about 100 cotton plants, at least about 500 cotton plants, at least about 1,000 cotton plants, at least about 5,000 cotton plants, at least about 10,000 cotton plants, at least about 100,000 cotton plants, at least about 500,000 cotton plants, at least about 1,000,000 cotton plants. Similarly, in certain aspects, the population of plants comprises 50 or more cotton plants, 100 or more cotton plants, 500 or more cotton plants, 1,000 or more cotton plants, 5,000 or more cotton plants, 10,000 or more cotton plants, 100,000 or more cotton plants, 500,000 or more cotton plants, or 1,000,000 or more cotton plants. The population may be grown under controlled conditions. In certain aspects, at least about 50%, 60%, 70%, 80%, 90%, 95%, 98%, or 99% of the plants in the population are at their reproductive stage. In certain aspects, at least about 50%, 60%, 70%, 80%, 90%, 95%, 98%, or 99% of the plants in the population produce seed. In certain aspects, the plant is a cotton plant and at least about 50%, 60%, 70%, 80%, 90%, 95%, 98%, or 99% of the cotton plants in the population have reached a stage in their life cycle wherein pinhead squares have formed.

In certain aspects, at least about 75%, 80%, 85%, 90%, 95%, 98%, or 99% of the plants in the population produce at least 20 seeds, at least 30 seeds, at least 40 seeds, at least 50 seeds, or at least 60 seeds. In certain aspects, at least about 75%, 80%, 85%, 90%, 95%, 98%, or 99% of the plants in the population are less than about 30 inches tall, less than about 24 inches tall, less than about 18 inches tall, less than about 15 inches tall, or less than about 12 inches tall. In certain aspects, the average height of the population is less than about 30 inches tall, less than about 24 inches tall, less than about 18 inches tall, less than about 15 inches tall, or less than about 12 inches tall.

Under normal commercial planting conditions, a cotton plant produces from about 18 to about 30 nodes, with the first fruiting node between node 5 and 9. When plants are grown under the stressed conditions disclosed herein, bolls typically set at nodes 5 or 6, one boll per plant.

Types of Plants

Unless otherwise specified, this disclosure is not limited to any particular type of plant. In certain aspects, the plant is a crop plant. Representative examples of crop plants include: a corn or maize plant, a soybean plant, a canola plant, a cotton plant, a wheat plant, and a sugarcane plant. In certain aspects, the plant is a cotton plant. In another aspect, a plant provided herein is selected from the group consisting of Acacia plant, an alfalfa plant, an aneth plant, an apple plant, an apricot plant, an artichoke plant, an arugula plant, an asparagus plant, an avocado plant, a banana plant, a barley plant, a bean plant, a beet plant, a blackberry plant, a blueberry plant, a broccoli plant, a Brussels sprout plant, a cabbage plant, a canola plant, a cantaloupe plant, a carrot plant, a cassava plant, a cauliflower plant, a celery plant, a Chinese cabbage plant, a cherry plant, a cilantro plant, a citrus plant, a clementine plant, a coffee plant, a corn plant, a cotton plant, a cucumber plant, a Douglas fir plant, an eggplant plant, an endive plant, an escarole plant, an *eucalyptus* plant, a fennel plant, a fig plant, a forest tree plant, a gourd plant, a grape plant, a grapefruit plant, a honey dew plant, a jicama plant, kiwifruit plant, a lettuce plant, a leek plant, a lemon plant, a lime plant, a Loblolly pine plant, a mango plant, a maple tree plant, a melon plant, a mushroom plant, a nectarine plant, a nut plant, an oat plant, an okra plant, an onion plant, an orange plant, an ornamental plant, a *papaya* plant, a parsley plant, a pea plant, a peach plant, a peanut plant, a pear plant, a pepper plant, a persimmon plant, a pine plant, a pineapple plant, a plantain plant, a plum plant, a pomegranate plant, a poplar plant, a potato plant, a pumpkin plant, a quince plant, a *radiata* pine plant, a radicchio plant, a radish plant, a rapeseed plant, a raspberry plant, a rice plant, a rye plant, a sorghum plant, a Southern pine plant, a soybean plant, a spinach plant, a squash plant, a strawberry plant, a sugar beet plant, a sugarcane plant, a sunflower plant, a sweet corn plant, a sweet potato plant, a sweetgum plant, a tangerine plant, a tea plant, a tobacco plant, a tomato plant, a turf plant, a vine plant, watermelon plant, a wheat plant, a yam plant, and a zucchini plant.

The plant may be any whole plant, or part of a plant, or tissue culture derived from a plant, or plant seed. In certain aspects, the plant is a cotton plant, a maize plant, or a soybean plant. A cotton plant for use in methods described herein can be at any of various developmental stages.

Table 1 describes different cotton developments stages.

TABLE 1

| | | Accumulated DD60s Heat Units | |
|---|---|---|---|
| Developmental Stage | Days | Previous Methods | New Methods* |
| Planting to Emergence | 4 to 9 | 50 to 60 | 76-171 |
| Emergence to First Square | 27 to 38 | 425 to 475 | 513-722 |
| Square to Flower | 20 to 25 | 300 to 350 | 380-475 |
| Planting to First Flower | 60 to 70 | 775 to 850 | 1140-1330 |

*based on a hypothetical example with consistent daily high temperatures of 90° F. (32.2° C.) and consistent daily low temperatures of 68° F. (20° C.).

DD60s are the accumulated heat units a plant receives each day and are determined by averaging each day's maximum and minimum temperatures and then subtracting 60, i.e. $DD60 = ((° F. \max + ° F. \min)/2) - 60$. The DD60s calculated for each day are added to determine the total DD60s for a given number of growing days.

Flower Timing

Figure 5:
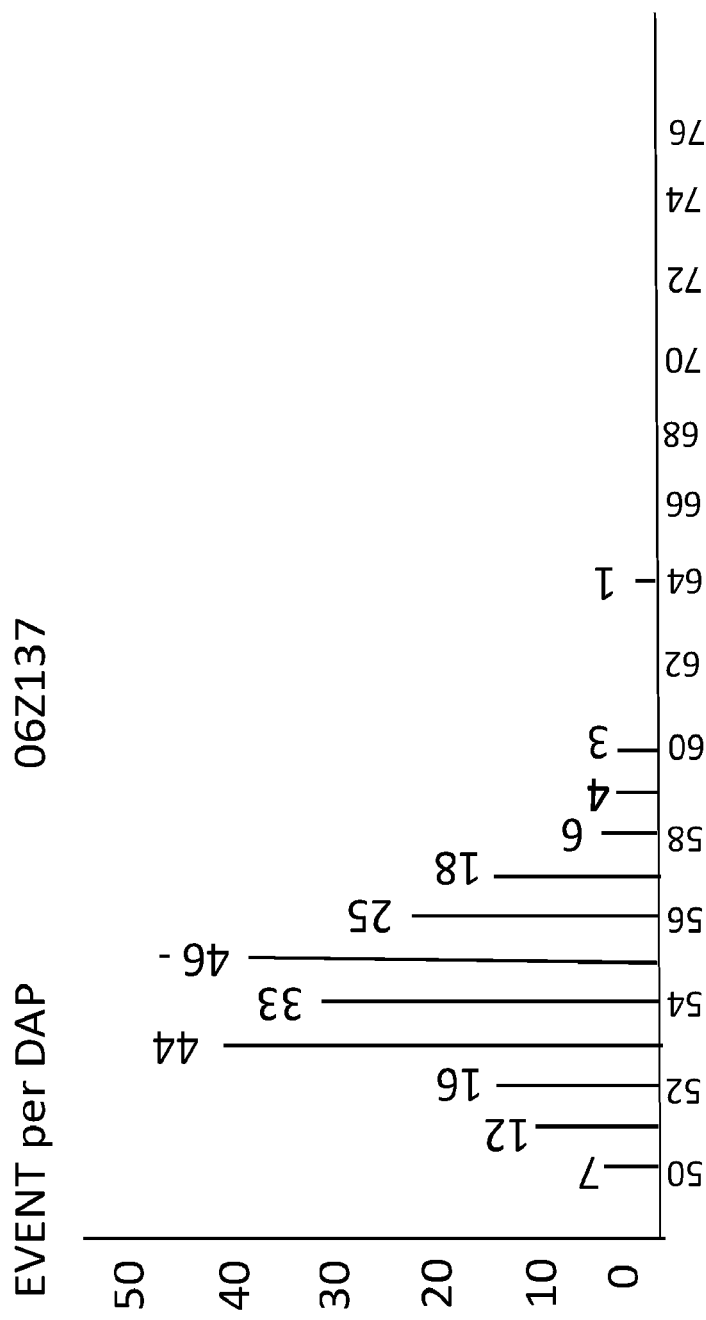
FIG. 5 shows distribution of flowering time as days after planting (DAP) in a population of cotton plants for several cotton lines.
Figure 5:
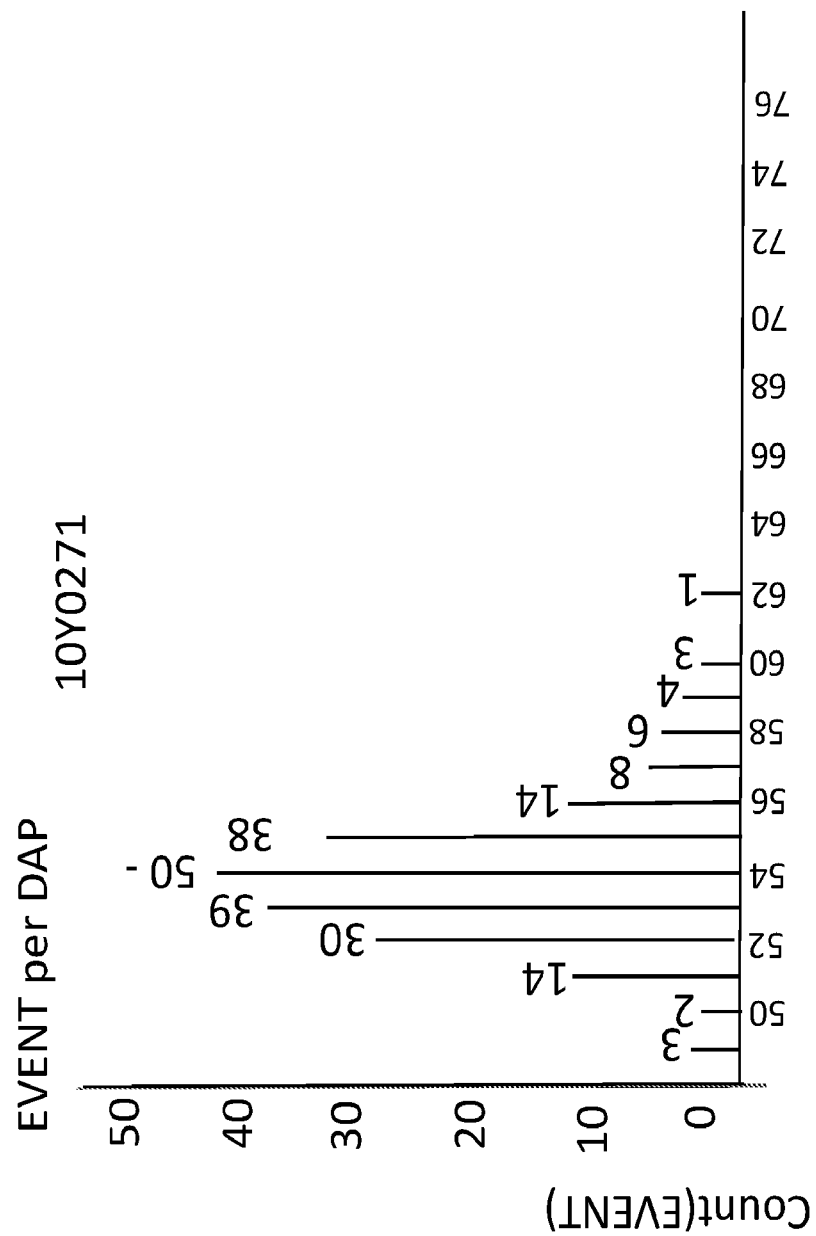
Figure 5:
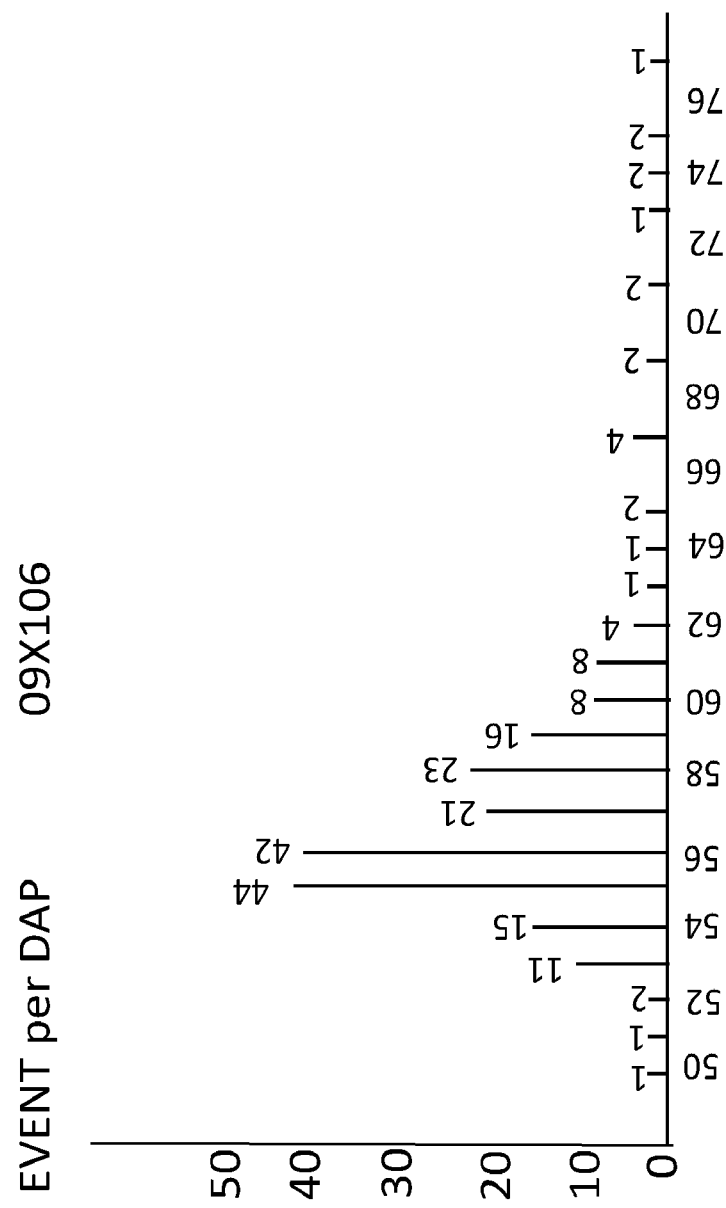
Figure 6:
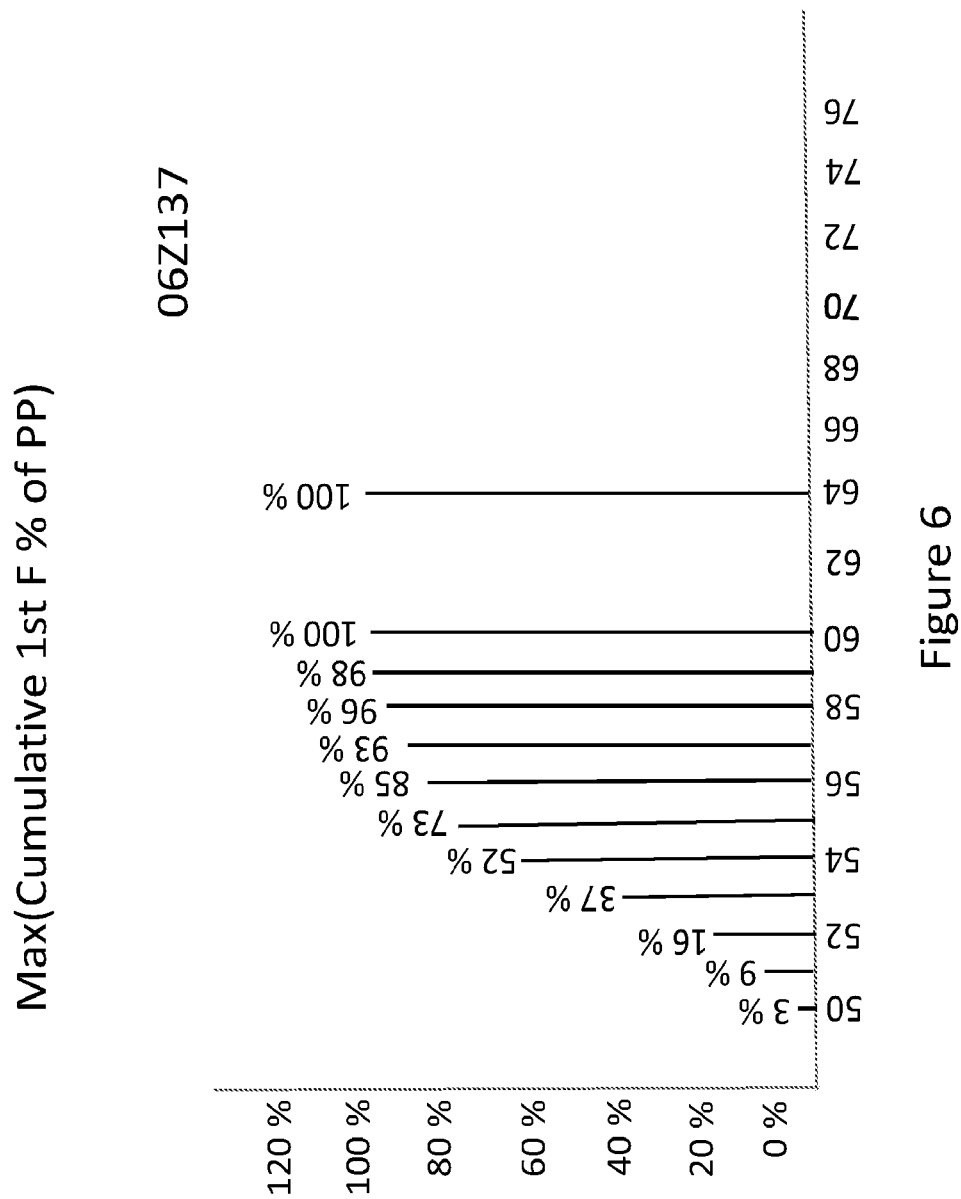
FIG. 6 shows the results disclosed in FIG. 5 as the cumulative % of plants that have flowered at DAP.
Figure 6:
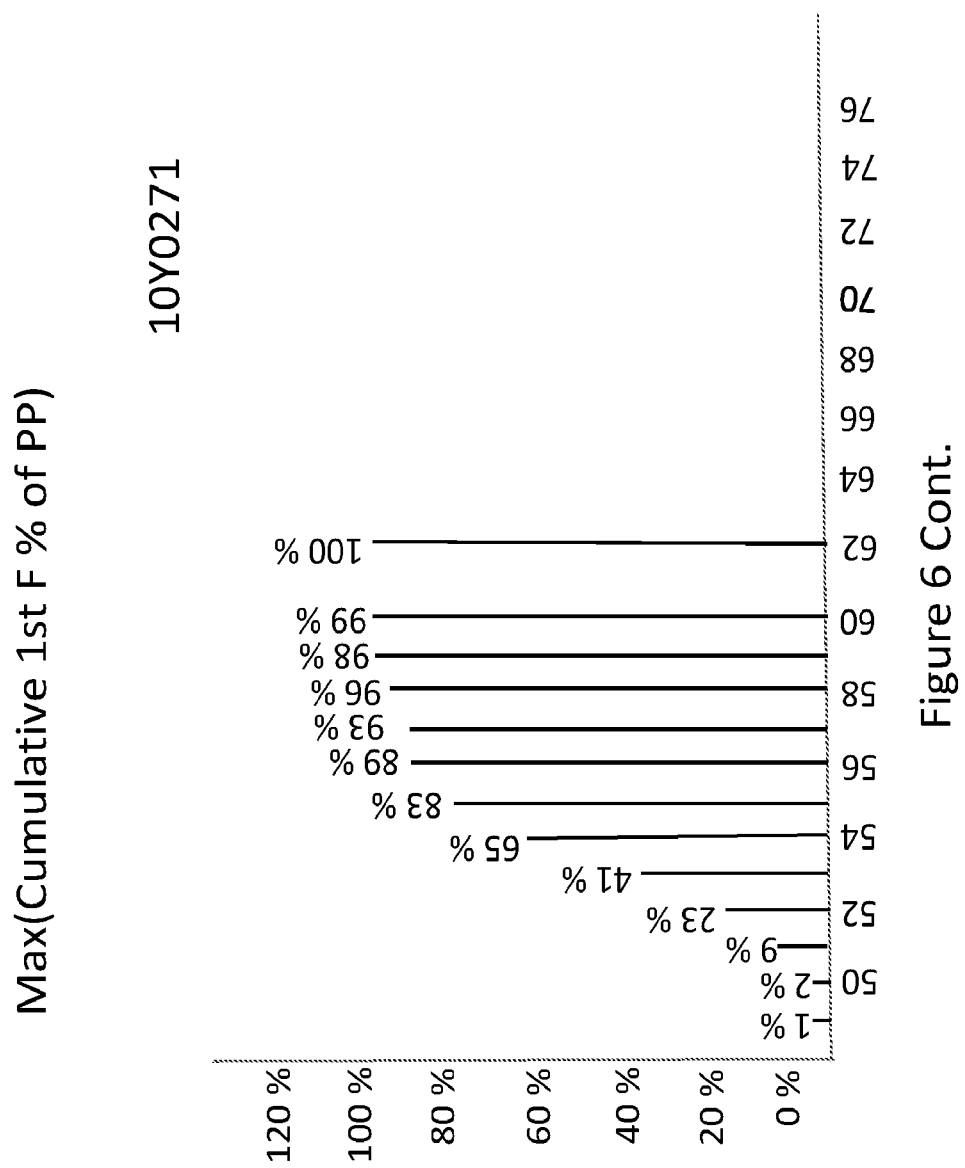
Figure 6:
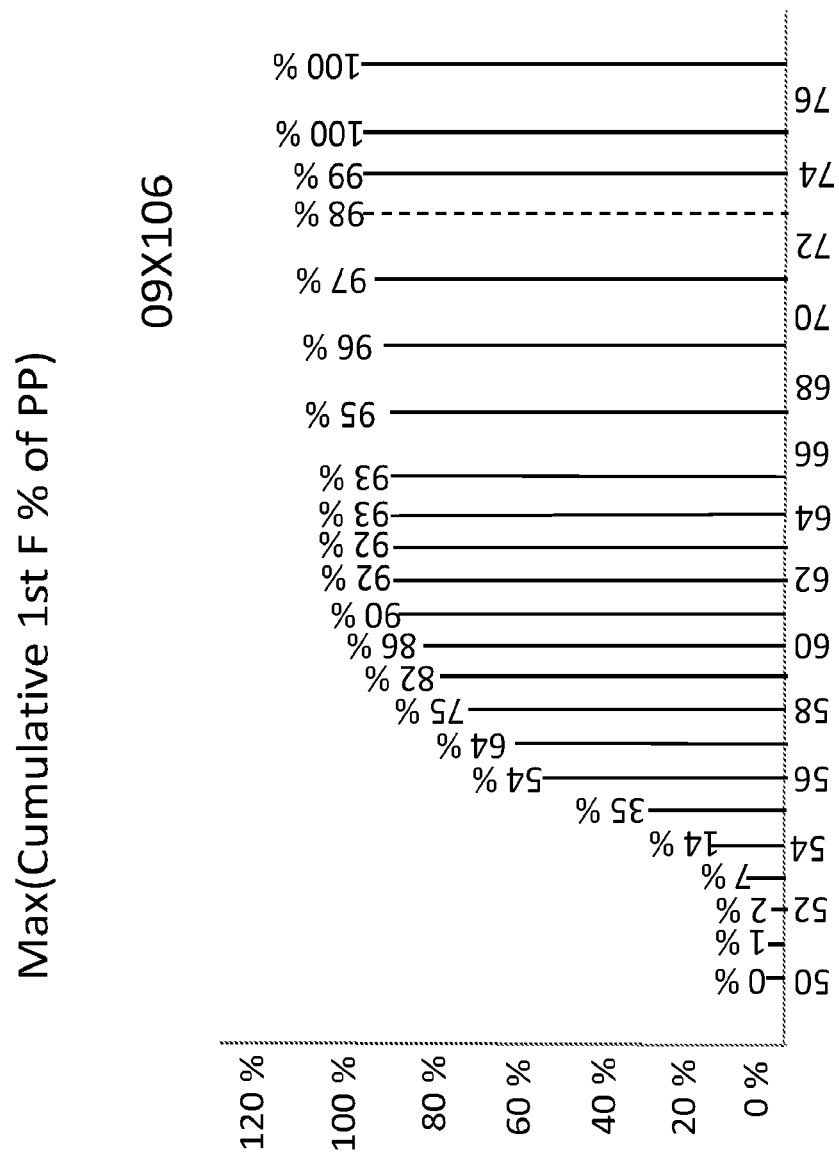

Within a population of plants, even for plants planted at the same time, the time at which they mature and/or start to flower and/or produce seeds is not necessarily simultaneous. For example, FIGS. 5 and 6 show a distribution of when standard cotton plants in a population start to flower, starting with just a small percentage in the first few days, then increasing over several days, and then the numbers tail off (FIG. 5) until 100% have flowered (cumulative shown in FIG. 6). In current methods of growing cotton plants under standard conditions, the time of flowering and seed maturation can be spread across a number of days or even weeks. Thus, this may require multiple rounds of gathering samples if it is desired to gather the samples at the same point of maturation throughout the population.

It has been discovered that for a population of plants grown according to methods utilizing the stressed conditions disclosed herein and/or having the resultant reduced statute morphology, the window of flowering time of the plants in the population is more synchronized (narrower) compared to control plants grown under standard conditions. That is, the window of time from when the first plants in the population begin to flower and/or produce seed and when a significant percentage, substantially all, or all of the plants in the population have flowered and/or produced seed is shorter. For example, in certain aspects, cumulatively 50%, 60%, 70%, 75%, 80%, 90%, 95%, 98%, 99%, or 100% of plants in a population of cotton plants disclosed herein have flowered and/or produced seed within 1 day, 2 days, 3 days, 4 days, 5 days, 6 days, 7 days, 8 days, 9 days, 10 days, 11 days, 12 days, 13 days, or 14 days from when the first plant in population flowers and/or produces seed. For example, in certain aspects, cumulatively 50%, 60%, 70%, 75%, 80%, 90%, 95%, 98%, 99%, or 100% of plants in a population of cotton plants disclosed herein have flowered and/or produced seed within 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, or 75 days after planting. In certain aspects, the timespan between when the first plant in a population of cotton plants begins to flower and/or produce seed and cumulatively 50%, 60%, 70%, 75%, 80%, 90%, 95%, 98%, 99%, or 100% of plants in a population have flowered and/or produced seed is 1%, 2%, 3%, 4%, 5%, 6%, 7%, 8%, 9%, 10%, 12%, 15%, 20%, 25%, 30%, 33%, 35%, 40%, 50%, 60%, 70%, 75%, or 80% less time in comparison to a control population of plants. As disclosed herein, the population of plants comprises at least about 50 cotton plants, at least about 100 cotton plants, at least about 500 cotton plants, at least about 1,000 cotton plants, at least about 5,000 cotton plants, at least about 10,000 cotton plants, at least about 100,000 cotton plants, at least about 500,000 cotton plants, at least about 1,000,000 cotton plants. Similarly, in certain aspects, the population of plants comprises 50 or more cotton plants, 100 or more cotton plants, 500 or more cotton plants, 1,000 or more cotton plants, 5,000 or more cotton plants, 10,000 or more cotton plants, 100,000 or more cotton plants, 500,000 or more cotton plants, or 1,000,000 or more cotton plants.

It is contemplated that tighter synchronization of maturation, flowering, and/or seed production timing will permit breeders to more consistently predict when plants in a population will flower and/or produce seeds. This reduced variability in developmental timing will improve operations and timing in, for example, industrial breeding programs, thereby reducing overall cycle time and resource waste.

EXAMPLES

The following examples are included to demonstrate certain aspects of the invention. It should be appreciated by those of skill in the art that the techniques disclosed in the examples which follow represent techniques discovered by the inventor to function well in the practice of the invention. However, those of skill in the art should, in light of the present disclosure, appreciate that many changes can be made in the specific aspects which are disclosed and still obtain a like or similar result without departing from the spirit and scope of the invention.

Example 1. Cotton Plants Grown Under High Stress and High Density

Approximately 188,000 plant pots, each comprising dimensions of approximately 7 cm wide×approximately 7 cm long×approximately 8 cm deep (for a total interior volume of slightly less than 400 mL) were assembled and prepared to receive growth media and seeds. Into each pot, approximately 380 mL of wet peat moss media was placed, along with Osmocote fertilizer following the manufacturer's recommendations. Into each pot, 2-3 F2 seeds of a certain cotton hybrid variety were planted.

Pots containing soil and seeds were then arranged into high-density growing blocs, each bloc comprising 324 pots in a 4.8 m$^2$ area. 580 of these blocs were squeezed into a shade house, such that a total of 187,920 pots comprised a total of 2,784 m$^2$ controlled environment space. The pots were arranged into this growing density immediately after seeds were planted and from that point on, the plants were subjected to the following temperature and irrigation stress conditions, in addition to the reduced soil volume and/or population density.

High Temperature.

Due to the prevailing climate of the latitude and region where the greenhouse was located (Costa Rica), the temperature variation in any 24-hour photocycle remained predictable throughout the growing period. During each 24-hour day, the temperatures would rise from nighttime lows of 18-22° C., rapidly reaching 30° C. in the morning when the greenhouse was in direct sun, and continuing to increase to an afternoon maximum of 35-45° C., which was maintained for at least 2-12 hours, each day. Temperatures dropped in the evenings, especially after the sunset, to eventually return to a nighttime low, which typically occurred between 1 a.m. and 4 a.m.

Reduced Irrigation.

Plants were irrigated via drip lines so that the volume of water accessible to the plant over any period of time could be carefully metered and controlled. Irrigation was provided through overhead sprinklers. To determine and control the amount of irrigation each plant received, several samples of plants were weighed before and after each irrigation. The weight gained was converted to volume of water and then divided by the total number of plants in the sample to determine the average amount of water each plant had received. Through careful weighing and sampling, this system was calibrated so that an average volume of water could be reliably, and verifiably, delivered to each plant in the covered environment. Through extensive testing across many growing cycles, it was discovered that approximately 100 mL of water per plant per 24-hour period was sufficient to keep the plant alive and induce the desired miniaturized morphology.

After approximately 3 days after planting (DAP), seedlings began to emerge from the pots. As emergence and growth proceeded, some pots produced more than one seedling (2-3 seeds were planted/pot to ensure at least one seedling/pot would be recovered), so additional seedlings were removed from those pots so that all pots produced only one seedling per pot ("doubles" and "triples" were culled down to singles). Thus, a total of 187,920 plants were now growing within a total of 2,784 m$^2$ within the controlled environment. During the next few days, plants were allowed to self-pollinate.

At 20 DAP, a plant treatment agent comprising mepiquat was applied. Approximately 0.5 L of PIX® per hectare was applied to the plants. Application comprised homogenizing 139 mL of PIX® in 20 L of water and loading the mixture into a backpack sprayer and then using the sprayer to apply the diluted PGR to the approximately 188,000 plants growing in the controlled environment. This same treatment was reapplied to the plants three more times in the following weeks, up until 60 DAP.

It was noted that the total volume of liquid added to the plants in any one day that the PGR was applied amounted to approximately 0.5 mL per plant, and so was considered a negligible amount of additional irrigation beyond the 100 mL that was meted out to each plant each day.

At approximately 25 DAP, at least one pinhead square appeared on all of the plants, typically at the 5$^{th}$ node. By 46-50 DAP, most plants had developed fully-formed flowers and by 60 DAP, all plants had flowers. Between 86-100 DAP, fully-mature bolls were harvested from the plants and the seeds within recovered. Seed yield was typically 20-30 seeds per boll.

In this example, at least 20 seeds were recovered from each of the 187,920 plants, all of which were cultivated within a 2,784 m$^2$ area of controlled environment. Producing seeds from this same number of crosses using current research methods, wherein cotton plants are typically planted at approximately 10 plant/m$^2$ in the field, would require approximately 18,800 m$^2$, or 1.8 hectares. Thus, the methods described herein allow one to produce seeds from the same number of crosses using only 10.5% of the growing area of current protocols.

Table 3a-g below shows data comparing field grown plants not subjected to stressed conditions in comparison to mini-cotton plants grown according to stressed conditions disclosed herein. At both early and late times, plants grown under the stressed conditions were significantly smaller in all aspects measured than field grown plants.

TABLE 2

| Treatment ID | PP | FINAL HARVEST | Final Harvest DAP | % HARVEST | Plant by m2 | Harv Plant m2 | Vol Pot (L) | Vol by M2 | Vol (L)/Harv Plant |
| --- | --- | --- | --- | --- | --- | --- | --- | --- | --- |
| 1-18 Standar-ST Irrigation-ST Osmocote | 324 | 320 | 115 | 99% | 67.5 | 66.67 | 0.4 | 27 | 0.41 |
| 2-400 mL POT-ST Irrigation-ST Osmocote | 360 | 344 | 115 | 96% | 75 | 71.67 | 0.35 | 26.25 | 0.37 |
| 3-400 mL POT-ST Irrigation-NewMixOsmocote | 360 | 316 | 115 | 88% | 75 | 65.83 | 0.35 | 26.25 | 0.40 |
| 4-18 Standar-ST Irrigation-NewMix Osmocote | 324 | 219 | 115 | 68% | 67.5 | 45.63 | 0.4 | 27 | 0.59 |
| 5-400 mL POT-Prog Irrigation-ST Osmocote | 360 | 340 | 115 | 94% | 75 | 70.83 | 0.35 | 26.25 | 0.37 |
| 6-400 mL POT-Prog Irrigation-NewMix Osmocote | 360 | 326 | 115 | 91% | 75 | 67.92 | 0.35 | 26.25 | 0.39 |
| 7-18 Standar-Prog Irrigation-NewMix Osmocote | 324 | 305 | 115 | 94% | 67.5 | 63.54 | 0.4 | 27 | 0.42 |
| 8-18 Standar-Prog Irrigation-ST Osmocote | 324 | 318 | 115 | 98% | 67.5 | 66.25 | 0.4 | 27 | 0.41 |
| 9-18 Standar-Field | 108 | 99 | 115 | 92% | 67.5 | 61.88 | 0.4 | 27 | 0.44 |
| 10-3 L Bag-Field | 100 | 89 | 115 | 89% | 50.4 | 44.86 | 2.8 | 141.12 | 3.15 |
| 11-3 L Bag-GHSE | 100 | 94 | 115 | 94% | 50.4 | 47.38 | 2.8 | 141.12 | 2.98 |
| 12-18 Standar-GHSE-NO PIX | 108 | 108 | 115 | 100% | 67.5 | 67.50 | 0.4 | 27 | 0.40 |
| 49-18 Standar-Black SEED_TRAY 100% CocoMix | 324 | 263 | 115 | 81% | 67.5 | 54.79 | 0.4 | 27 | 0.49 |
| 50-18 Standar-Fuzzy SEED_TRAY 100% CocoMix | 324 | 314 | 115 | 97% | 67.5 | 65.42 | 0.4 | 27 | 0.41 |
| 51-18 Standar-High Density | 648 | 547 | 115 | 84% | 100 | 84.41 | 0.4 | 40 | 0.47 |

TABLE 3 a

| | Row Labels | Days After Planting (DAP) | Number of Plants | | Average of Height from Cotyledon to Last open leaf (cm) |
| --- | --- | --- | --- | --- | --- |
| Early | Field plant-PIX application | 34 | 10 | Field plant-PIX application | 21.95 |
| | Mini plants-PIX application | 17 | 5 | Mini plants-PIX application | 9.8 |
| Late | Field Plant-Near Cut off | 86 | 5 | Field Plant-Near Cut off | 162.4 |
| | Mini Plant Harvest | 119 | 5 | Mini Plant Harvest | 29.3 | b

| | | Average of # Nodes | | Average of # Bolls |
| --- | --- | --- | --- | --- |
| Early | Field plant-PIX application | 8.7 | Field plant-PIX application | n/a |
| | Mini plants-PIX application | 3 | Mini plants-PIX application | n/a |
| Late | Field Plant-Near Cut off | 26.8 | Field Plant-Near Cut off | 21.2 |
| | Mini Plant Harvest | 8.6 | Mini Plant Harvest | 1.2 | c

| | | Average of 1st Node with boll | | Average of Weight from N0 and up (grams) |
| --- | --- | --- | --- | --- |
| Early | Field plant-PIX application | 5.4 | Field plant-PIX application | 25.67 |
| | Mini plants-PIX application | 0 | Mini plants-PIX application | 6.2 |
| Late | Field Plant-Near Cut off | 5.6 | Field Plant-Near Cut off | 1028 |
| | Mini Plant Harvest | 5.6 | Mini Plant Harvest | 18.1 |

TABLE 3-continued d

| | | Average of Flowers/Fruits-Fresh Weight at site (grams) | | Average of Flowers/Fruits-Dry Weight at lab (grams) |
|---|---|---|---|---|
| Early | Field plant-PIX application | 0.21 | Field plant-PIX application | 0.045 |
| | Mini plants-PIX application | 0 | Mini plants-PIX application | 0 |
| Late | Field Plant-Near Cut off | 307.44 | Field Plant-Near Cut off | 46.6 |
| | Mini Plant Harvest | 6.58 | Mini Plant Harvest | 5.55 | e

| | | Average of Leaves-Fresh Weight at site (grams) | | Average of Leaves-Dry Weight at lab (grams) |
|---|---|---|---|---|
| Early | Field plant-PIX application | 18.72 | Field plant-PIX application | 2.679 |
| | Mini plants-PIX application | 3.68 | Mini plants-PIX application | 0.14 |
| Late | Field Plant-Near Cut off | 281.84 | Field Plant-Near Cut off | 65.9 |
| | Mini Plant Harvest | 5.92 | Mini Plant Harvest | 1.296 | f

| | | Average of Stem-Fresh Weight at site (grams) | | Average of Stem-Dry Weight at lab (grams) |
|---|---|---|---|---|
| Early | Field plant-PIX application | 4.91 | Field plant-PIX application | 0.363 |
| | Mini plants-PIX application | 0.74 | Mini plants-PIX application | 0.062 |
| Late | Field Plant-Near Cut off | 342.16 | Field Plant-Near Cut off | 90.66 |
| | Mini Plant Harvest | 5.16 | Mini Plant Harvest | 1.704 | g

| | | Ave. dry weight total (grams) (sum of above dry weights) |
|---|---|---|
| Early | Field plant-PIX application | 3.087 |
| | Mini plants-PIX application | 0.202 |
| Late | Field Plant-Near Cut off | 203.16 |
| | Mini Plant Harvest | 8.55 |

What is claimed is:

1. A method of generating a population of cotton plants with an altered morphology, the method comprising:
   sowing cotton seeds and allowing them to germinate;
   growing the seeds into a population of cotton plants at an average density of at least 10 plants per square meter in a controlled environment wherein the plants of the population are grown at the density in an average volume of growth media of less than about 1,000 mL per plant, and
   wherein the method comprises exposing the cotton plants to heat stress and/or water shortage for an extended period of time,
   thus generating the population of cotton plants with an altered morphology wherein at least about 70% of the individual cotton plants in the population are between about 12 inches and 24 inches tall and have at least one boll that contains at least 20 seeds.

2. The method of claim 1, wherein the method comprises growing the cotton plants at a temperature of at least about 36° C. for at least about 2 hours per day, for at least 50 days during the time from the average day of germination of the cotton seeds of the population to the average day that the plants produce at least one cotton boll that contains a seed.

3. The method of claim 1, wherein the method comprises growing the cotton plants while providing less than about 400 mL of water per day on average, for at least 50 days during the time from the average day of germination of the cotton seeds of the population to the average day that the plants produce at least one cotton boll that contains a seed.

4. The method of claim 1, wherein the method comprises growing the cotton plants at a temperature of at least about 36° C. for at least about 2 hours per day, for at least 50 days during the time from the average day of germination of the cotton seeds of the population to the average day that the plants produce at least one cotton boll that contains a seed and growing the cotton plants while providing less than about 400 mL of water per day on average, for at least 50 days during the time from the average day of germination of the cotton seeds of the population to the average day that the plants produce at least one cotton boll that contains a seed.

5. The method of claim 1, wherein the population of plants is grown at an average density of at least 30 plants per square meter.

6. The method of claim 1, wherein the plants of the population are grown at the density in an average volume of growth media of less than about 500 mL per plant.

7. The method of claim 2, comprising growing the population of cotton plants at a temperature of at least about 37° C. for at least about 2 hours per day, for at least 50 days during the time from the average day of germination of the cotton seeds of the population to the average day that the plants produce at least one cotton boll that contains a seed.

8. The method of claim 3, comprising growing the population of cotton plants while providing less than about 300 mL of water per day on average, for at least 50 days during the time from the average day of germination of the cotton seeds of the population to the average day that the plants produce at least one cotton boll that contains a seed.

9. The method of claim 1, wherein at least about 80% of the individual cotton plants in the population are between about 12 inches and 24 inches tall and have at least one boll that contains at least 20 seeds.

10. The method of claim 1, wherein the population comprises at least about 1,000 cotton plants.

11. The method of claim 1, wherein the controlled environment is substantially free of pollinating insects.

12. The method of claim 1, wherein the method further comprises applying a plant growth regulator selected from the group consisting of chlormequat-CL, mepiquat-CL, AMO-1618, clorphonium-Cl, tetcylacis, ancymidol, flurprimidol, paclobutrazol, uniconazole-P, inabenfide, prohexadione-CA, trinexapac-ethyl, daminozide, exo-16,17-, dihydro-GA5-13-acetate, systemin, phytosulfokine, and rapid alkalinization factor; wherein the plant growth regulator is applied at a day not past 25 days after germination.

* * * * *